United States Patent
Brockway et al.

(10) Patent No.: US 9,414,786 B1
(45) Date of Patent: *Aug. 16, 2016

(54) ECG SENSING WITH NOISE FILTERING

(71) Applicant: VivaQuant LLC, St. Paul, MN (US)

(72) Inventors: Marina Brockway, St. Paul, MN (US); Brian Brockway, St. Paul, MN (US)

(73) Assignee: VivaQuant LLC, St. Paul, MN (US)

(*) Notice: Subject to any disclaimer, the term of this patent is extended or adjusted under 35 U.S.C. 154(b) by 115 days.

This patent is subject to a terminal disclaimer.

(21) Appl. No.: 14/032,544

(22) Filed: Sep. 20, 2013

Related U.S. Application Data

(63) Continuation-in-part of application No. 13/293,632, filed on Nov. 10, 2011, now Pat. No. 8,543,195, which is a continuation-in-part of application No. 12/938,995, filed on Nov. 3, 2010, now Pat. No. 8,632,465.

(60) Provisional application No. 61/412,108, filed on Nov. 10, 2010, provisional application No. 61/257,718, filed on Nov. 3, 2009, provisional application No. 61/366,052, filed on Jul. 20, 2010.

(51) Int. Cl.
*A61B 5/0402* (2006.01)
*A61B 5/00* (2006.01)
*A61B 5/04* (2006.01)
*A61B 5/0408* (2006.01)

(52) U.S. Cl.
CPC ............ *A61B 5/7203* (2013.01); *A61B 5/0006* (2013.01); *A61B 5/0402* (2013.01); *A61B 5/04012* (2013.01); *A61B 5/04087* (2013.01)

(58) Field of Classification Search
CPC .. A61B 5/0432; A61B 5/0402; A61B 5/0424; A61B 5/0408–5/04016; A61B 5/7203; A61B 5/0006; A61B 5/04087; A61B 5/04017; A61B 5/0452; A61B 5/7253; H03H 17/0248
USPC .......................... 600/523, 300, 508, 509, 522
See application file for complete search history.

(56) References Cited

U.S. PATENT DOCUMENTS

| | | |
|---|---|---|
| 5,090,418 A | 2/1992 | Squires et al. |
| 5,521,851 A | 5/1996 | Wei et al. |

(Continued)

FOREIGN PATENT DOCUMENTS

WO  2013/043157 A2  3/2013

OTHER PUBLICATIONS

Figueredo et al. Compression of Electrocardiogram Using Neural Networks and Wavelets. Computer and Information Science Studies in Computational Intelligence. vol. 131, 2008, pp. 27-40.*

(Continued)

*Primary Examiner* — Christopher D Koharski
*Assistant Examiner* — Jeremiah Kimball
(74) *Attorney, Agent, or Firm* — Crawford Maunu PLLC

(57) ABSTRACT

Various embodiments are directed to signal processing. In accordance with example embodiments, methods and apparatuses involve using at least two electrodes that sense an ECG signal. A denoising module is communicatively coupled to the at least two electrodes, and receives the ECG signal sensed by the sensing electrodes. The denoising module includes circuitry that conditions and digitizes the ECG signal, and a computing circuit that processes the digitized ECG signal to denoise the ECG signal. A communications circuit generates a communication including the denoised ECG signal for access by a remote device.

21 Claims, 11 Drawing Sheets

(56) References Cited

U.S. PATENT DOCUMENTS

| | | | |
|---|---|---|---|
| 5,776,073 A * | 7/1998 | Garfield et al. | 600/546 |
| 5,792,065 A | 8/1998 | Xue et al. | |
| 5,817,027 A | 10/1998 | Arand et al. | |
| 5,827,195 A | 10/1998 | Lander | |
| 5,987,352 A | 11/1999 | Klein et al. | |
| 6,117,077 A * | 9/2000 | Del Mar | A61B 5/04085 600/300 |
| 6,389,308 B1 | 5/2002 | Shusterman | |
| 6,589,189 B2 | 7/2003 | Meyerson et al. | |
| 6,690,959 B2 | 2/2004 | Thompson | |
| 6,701,170 B2 | 3/2004 | Stetson | |
| 6,822,564 B2 | 11/2004 | Al-Ali | |
| 6,856,832 B1 * | 2/2005 | Matsumura et al. | 600/523 |
| 7,096,060 B2 | 8/2006 | Arand et al. | |
| 7,099,714 B2 * | 8/2006 | Houben | A61B 5/0031 600/509 |
| 7,115,096 B2 | 10/2006 | Siejko et al. | |
| 7,236,819 B2 | 6/2007 | Brockway et al. | |
| 7,272,265 B2 | 9/2007 | Kouri et al. | |
| 7,376,453 B1 | 5/2008 | Diab et al. | |
| 7,602,985 B2 * | 10/2009 | Gao et al. | 382/240 |
| 7,627,369 B2 | 12/2009 | Hunt | |
| 7,672,717 B1 * | 3/2010 | Zikov | A61B 5/0476 600/509 |
| 7,840,259 B2 | 11/2010 | Xue et al. | |
| 8,086,304 B2 | 12/2011 | Brockway et al. | |
| 8,201,330 B1 | 6/2012 | Rood et al. | |
| 8,214,007 B2 | 7/2012 | Baker et al. | |
| 8,271,073 B2 | 9/2012 | Zhang et al. | |
| 8,348,852 B2 | 1/2013 | Bauer et al. | |
| 8,460,189 B2 * | 6/2013 | Libbus et al. | 600/301 |
| 8,478,389 B1 * | 7/2013 | Brockway | A61B 5/7203 600/509 |
| 8,543,195 B1 * | 9/2013 | Brockway et al. | 600/509 |
| 9,095,266 B1 * | 8/2015 | Fu | A61B 5/0476 600/544 |
| 2003/0185408 A1 * | 10/2003 | Causevic | A61B 5/04845 381/94.1 |
| 2004/0138578 A1 * | 7/2004 | Pineda | A61M 21/00 600/544 |
| 2005/0010120 A1 | 1/2005 | Jung et al. | |
| 2005/0234361 A1 | 10/2005 | Holland | |
| 2005/0265629 A1 * | 12/2005 | Fu | G06K 9/00516 382/275 |
| 2005/0283090 A1 | 12/2005 | Wells | |
| 2006/0094992 A1 * | 5/2006 | Imboden et al. | 601/70 |
| 2007/0219453 A1 | 9/2007 | Kremliovsky et al. | |
| 2007/0219455 A1 | 9/2007 | Wong et al. | |
| 2007/0260151 A1 | 11/2007 | Clifford | |
| 2007/0265508 A1 | 11/2007 | Sheikhzadeh-Nadjar | |
| 2008/0065158 A1 | 3/2008 | Ben-Ezra et al. | |
| 2008/0097537 A1 | 4/2008 | Duann et al. | |
| 2008/0183093 A1 | 7/2008 | Duann et al. | |
| 2008/0200832 A1 | 8/2008 | Stone | |
| 2009/0069703 A1 | 3/2009 | Takla et al. | |
| 2009/0222262 A1 | 9/2009 | Kim et al. | |
| 2010/0063438 A1 * | 3/2010 | Bengtsson | A61M 5/14248 604/66 |
| 2011/0306895 A1 * | 12/2011 | Nakashima | A61B 5/04017 600/544 |
| 2012/0165691 A1 | 6/2012 | Ting et al. | |
| 2012/0197144 A1 | 8/2012 | Christ et al. | |
| 2012/0232417 A1 | 9/2012 | Zhang | |
| 2013/0069768 A1 * | 3/2013 | Madhyastha et al. | 340/12.5 |
| 2013/0109937 A1 | 5/2013 | Banet et al. | |
| 2013/0289424 A1 * | 10/2013 | Brockway et al. | 600/509 |
| 2014/0005988 A1 | 1/2014 | Brockway | |

OTHER PUBLICATIONS

Tsalaile, et al. "Blind Source Extraction of Heart Sound Signals From Lung Sound Recordings Exploiting Periodicity of the Heart Sound," ICASSP 2008 IEEE, p. 461-464.

Jungwirth B, Mackensen GB, Blobner M, Neff F, Reichart B, Kochs EF, Nollert G: Neurologic outcome after cardiopulmonary bypass with deep hypothermic circulatory arrest in rats: description of a new model. J Thorac Cardiovasc Surg 2006, 131:805-812.

Kellermann, et al.,"A mobile phone based alarm system for supervising vital parameters in free moving rats," BMC Research Notes 2012, 5:119, Feb. 23, 2012.

http://www.simplehelp. net/2006/09/12/how-to-set-up-outlook-2003-for-email/.

B. Widrow, et al., "Adaptive noise cancelling: principles and applications," IEEE Proc., vol. 63, No. 12, pp. 1692-1716, Dec. 1975.

H. Boudoulas, YH. Sohn, W. O'Neill, R. Brown, AM. Weissler. The QT greater that QS2 syndrome: a new mortality risk indicator in coronary artery disease. American Journal of Cardiology, vol. 50 (6) pp. 1229-1235 (1982).

G. Moody, W. Muldrow, and R. Mark, "A noise stress test for arrhythmia detectors," Computers in Cardiology, pp. 381-384 (1984).

K. R. Rao and P. Yip, "Discrete Cosine Transform: Algorithms, Advantages, Applications," San Diego, CA: Academic (1990).

J. Woods. Subband Coding, Kluwer Academic Press (1990).

K. Ball, L. Sirovich, and L. Keefe, "Dynamical Eigenfunction Decomposition of Turbulent Channel Flow," International Journal for Numerical Methods in Fluids, vol. 12, Issue 6, pp. 585-604 (Apr. 1991).

NV Thakor and YS Zhu, "Applications of adaptive filtering to ECG analysis: noise cancellation," IEEE Transactions on Biomedical Engineering, vol. 38, No. 8, pp. 785-794 (Aug. 1991).

S. Mallat and W. L.-Hwang, "Singularity Detection and Processing with Wavelets," IEEE Transactions on Information Technology (38), pp. 617-643 (1992).

S. Mallat and S. Zhong, "Characterization of Signals from Multiscale Edges," IEEE Trans. Pattern Anal. Mach. Intell. 14, 7 (Jul. 1992).

Vaidyanathan, Multirate Systems and Filter Banks, Prentice Hall, 1993.

Y. Pati, R. Rezaiifar and P. Krishnaprasad, "Orthogonal Matching Pursuit: Recursive Function Approximation With Applications to Wavelet Decomposition," in Asilomar Conference on Signals, Systems and Computers, vol. 1, pp. 40-44 (Nov. 1993).

S. Mallat and Z. Zhang, "Matching Pursuits with Time-Frequency Dictionaries," IEEE TSP(41), No. 12, pp. 3397-3415 (Dec. 1993).

P. Comon, "Independent component analysis, a new concept?," Signal Process. Special Issue on Higher Order Statistics, vol. 36, No. 3, pp. 287-314 (Apr. 1994).

Donoho, D.L., I.M. Johnstone (1994), "Ideal spatial adaptation by wavelet shrinkage," Biometrika, vol. 81, pp. 425-455.

Y. Xu, J. Weaver, D. Healy, Jr. And J. Lu, "Wavelet Transform Domain Filters: A Spatially Selective Noise Filtration Technique," IEEE Transactions on Image Processing, vol. 3, No. 6, pp. 747-758 (1994).

D. L. Donoho, "Denoising by Soft-Thresholding," IEEE Trans. on Inf. Theory, vol. 41, No. 3, pp. 613-627 (May 1995).

A.Bell and T. Sejnowski, "An Information-Maximization Approach to Blind Separation and Blind Deconvolution," Neural Computation, 7:1129-1159. (1995).

M. Haugland and T. Sinkjaer, "Cutaneous Whole Nerve Recordings Used for Correction of Footdrop in Hemiplegic Man," IEEE Transactions on Rehabilitation Engineering, vol. 3, No. 4. pp. 207-317 (Dec. 1995).

V. Afonso, W. Tompkins, T. Nguyen, K. Michler and S. Luo, "Comparing Stress ECG Enhancement Algorithms," IEEE in Medicine and Biology, Engineering Biology, pp. 37-44 (May/Jun. 1996).

J. Francois Cardoso, "Infomax and Maximum Likelihood for Source Separation," IEEE Letters on Signal Processing, vol. 4, No. 4, pp. 112-114 (Apr. 1997).

M. L. Hilton, "Wavelet and Wavelet Packets Compression of Electrocardiogram," IEEE Transactions on Biomedical Engineering, vol. 44, No. 5, pp. 394-402 (May 1997).

A. Hyvärinen, "New Approximations of Differential Entropy for Independent Component Analysis and Projection Pursuit," In Advances in Neural Information Processing Systems, vol. 10, pp. 273-279, MIT Press. (1997).

W. Sweldens. The lifting scheme: A construction of second generation wavelets. SIAM J. Math. Anal., 29(2):511-546, 1997.

(56) References Cited

OTHER PUBLICATIONS

American National Standard ANSI/AAMI EC57:1998, Testing and Reporting Performance Results of Cardiac Rhythm and ST Segment Measurement Algorithms.

Testing and reporting performance results of cardiac rhythm and ST-segment measurement algorithms ANSI/AAMI EC57:1998.

L. Torres-Pereira, et. al. "A Biotelemetric Heart Sound Monitoring System," in Proceedings of the 14th International Symposium on Biotelemetry. Marburg, 1998.

A. Hyvärinen, "Fast and Robust Fixed-Point Algorithms for Independent Component Analysis," IEEE Transactions on Neural Networks, vol. 10, No. 3, pp. 626-634 (May 1999).

J.-F. Cardoso, "High-Order Contrasts for Independent Component Analysis," Neural Comput., vol. 11, No. 1, pp. 157-192 (1999).

S. Chen, D Donoho, and M. Saunders, "Atomic Decomposition by Basis Pursuit," SIAM J. Scientific Computing, vol. 20, No. 1, pp. 33-61 (1999).

Q. Pan, L. Zhang, G. Dai and H. Zhang, "Two Denoising Methods by Wavelet Transform," IEEE Trans. on SP, vol. 47, No. 12, pp. 3401-3406 (Dec. 1999).

G. Michaud, Q. Li, X. Costeas, R. Stearns, M. Estes, and PJ Wang, "Correlation waveform analysis to discriminate monomorphic ventricular tachycardia from sinus rhythm using stored electrograms from implantable defibrillators," PACE. Aug. 1999; 22(8):1146-51 (1999).

S. Mallat, "A Wavelet Tour of Signal Processing," Academic Press, 1999.

Langley, P.; Di Bernardo, D.; Murray, A.; Comparison of three measures of QT dispersion. Computers in Cardiology 1999 pp. 69-72.

Goldberger AL et al. PhysioBank, PhysioToolkit, and PhysioNet: components of a new research resource for complex physiologic signals. Circulation 101(23): e215-e220, (Jun. 13, 2000).

Z. Lu, D. Kim, and W. Pearlman, "Wavelet Compression of ECG Signals by the Set Partitioning in Hierarchical Trees Algorithm," IEEE Transactions on Biomedical Engineering, vol. 47, No. 7, pp. 849-856 (Jul. 2000).

M. Marcellin, M. gormish, A. Bilgin and M. Boleik, "An Overview of JPEG-2000," Proc. of IEEE Data Compression Conference, pp. 523-541 (2000).

L. K. Saul and J. B. Allen, "Periodic component analysis: An eigenvalue method for representing periodic structure in speech," in NIPS, [Online]pp. 807-813 (2000). Available: http://www.cs.cmu.edu/Groups/NIPS/00papers-pub-on-web/SaulAllen.pdf.

C. Taswell, "The What, How, and Why of Wavelet Shrinkage Denoising," Computing in Science and Engineering, vol. 2, No. 3, pp. 12-19 (2000).

J. S. Richman and J. R. Moorman, Physiological time-series analysis using approximate entropy and sample entropy Am. J. Physiol. 278, H2039 (2000).

K. Sayood, "Introduction to Data Compression," Academic Press 2000.

Malik M, Batchvarov VN. Measurement, interpretation and clinical potential of QT dispersion. J Am Coll Cardiol. Nov. 15, 2000;36(6):1749-66.

A. Hyvärinen and E. Oja, "Independent Component Analysis: Algorithms and Applications," Neural Networks, 13(4-5), pp. 411-430 (2000).

R. Mayerburg. Sudden cardiac death: exploring the limits of our knowledge. Journal of Cardiovascular Electrophysiology, vol. 12, No. 3, Mar. 2001.

M. Brennan, M. Palaniswami, and P. Kamen. Do Existing Measures of Poincare Plot Geometry Reflect Nonlinear Features of Heart Rate Variability? IEEE Transactions on Biomedical Engineering, vol. 48, No. 11, Nov. 2001.

D. Donoho and X. Huo, "Uncertainty Principles and Ideal Atomic Decomposition," IEEE Transactions on Information Theory, vol. 47, No. 7, pp. 2845-2862 (Nov. 2001).

M. Zibulevsky and B. Pearlmutter, "Blind Source Separation by Sparse Decomposition in A Signal Dictionary," Neural Computation. vol. 13, pp. 863-882 (2001).

Oweiss, K.G. Anderson, D.J. "MASSIT—Multiresolution Analysis of Signal Subspace Invariance Technique: a novel algorithm for blind source separation", Conference on Signals, Systems and Computers Publication Date: 2001 vol. 1, pp. 819-823 vol. 1.

M. Costa, A. L. Goldberger, and C.-K. Peng, Multiscale Entropy Analysis of Complex Physiologic Time Series, Phys. Rev. Lett. 89, 6, (2002).

B. U. Kohler, C. Hennig, R. Orglmeister. The principles of software QRS detection. IEEE Engineering in Medicine and Biology Magazine, vol. 21, No. 1. (2002), pp. 42-57.

G.-J. Jang, T.-W. Lee and Y.-H Oh, "Single-Channel Signal Separation Using Time-Domain Basis Functions," IEEE Signal Processing Letters, vol. 10, No. 6, pp. 168-171 (Jun. 2003).

T. Blaschke and L. Wiskott, "Cubica: Independent Component Analysis by Simultaneous Third- and Fourth-Order Cumulant Diagonalization," IEEE Transactions on Signal Processing, vol. 52, No. 5, pp. 1250-1256 (May 2004).

D A Clunie, "Extension of an open source DICOM toolkit to support SCP-ECG waveforms," 2nd OpenECG Workshop 2004, Berlin, Germany.

J.-P Martinez, et. al., "A wavelet-based ECG delineator: Evaluation on standard databases," IEEE transactions on biomedical engineering, vol. 51, No. 4, pp. 57 (2004).

Thomsen, M. B., Verduyn, S. C., Stengl, M., Beekman, J. D., de Pater, G., van Opstal, J., et al. (2004). Increased short-term variability of repolarization predicts d- sotalolinduced torsade de pointes in dogs. Circulation, 110, 2453-2459.

Malik M, Hnatkova K, Batchvarov V, Gang Y, Smetana P, Camm AJ. Sample size, power calculations, and their implications for the cost of thorough studies of drug induced QT interval prolongation. Pacing Clin Electrophysiol. Dec. 2004;27(12):1659-69.

Madalena Costa.et. al. Multiscale entropy analysis of biological signals. Physical Review E 71, 021906 s2005d.

M. Alghoniemy and A. Tewfik, "Reduced Complexity Bounded Error Subset Selection," IEEE Int. Conf. Acoustics, Speech and Signal Processing (ICASSP), pp. 725-728 (Mar. 2005).

S.-C. Tai, C.-C. Sun and W.-C Yan, "2-D ECG Compression Method Based on Wavelet Transform and Modified SPIHT," IEEE Trans. Biomed. Eng., vol. 52, No. 6, pp. 999-1008 (Jun. 2005).

Hamlin RL. Non-drug-related electrocardiographic features in animal models in safety pharmacology. J Pharmacol Toxicol Methods. Jul.-Aug. 2005; 52(1): 60-76.

HJ van der Linde, A van Water, W Loots, B van Dueren, K van Ammel, M Peters and DJ Gallacher. A new method to calculate the beat-to-beat instability of QT duration in drug-induced long QT in anesthetized dogs. Journal of Pharmacological and Toxicological Methods 52 (2005) 168-177.

R. Sameni, MB Shamsollahi, C. Jutten, and M. Babaie-Zadeh, "Filtering Noisy ECG Signals Using the Extended Kalman Filter Based on a Modified Dynamic ECG Model," Computers in Cardiology, pp. 1017-1020 (2005).

M. Blanco-Velasco, B. Weng and KE Barner, "A New ECG Enhancement Algorithm for Stress ECG Tests," Computers in Cardiology, vol. 33, pp. 917-920 (2006).

Chen PC, Lee S, Kuo CD. Delineation of T-wave in ECG by wavelet transform using multiscale differential operator. IEEE Trans Biomed Eng. Jul. 2006;53(7):1429-33.

K. Zhang, L.-W. Chan, "An Adaptive Method for Subband Decomposition ICA", Neural Computation, vol. 18, No. 1, pp. 191-223 (2006).

R. Brychta, "Wavelet analysis of autonomic and cardiovascular signals," PhD Dissertation. Vanderbilt University (Aug. 2006).

M. Aminghafari, N. Cheze, J.-M Poggi, "Multivariate de-noising using wavelets and principal component analysis," Computational Statistics & Data Analysis, 50, pp. 2381-2398 (2006).

Aharon, M. Elad and A. Bruckstein, "K-SVD: An Algorithm for Designing Overcomplete Dictionaries for Sparse Representation," IEEE Transactions on Signal Processing, vol. 54, No. 11, pp. 4311-4322 (Nov. 2006).

Chouakri S.A., et al. ECG signal smoothing based on combining wavelet denoising levels. Asian Journal of Information Technology. vol. 5, pp. 667-677. 2006.

(56) References Cited

OTHER PUBLICATIONS

Inan, O.T.; Giovangrandi, L.; Kovacs, G.T.A.; Robust Neural-Network-Based Classification of Premature Ventricular Contractions Using Wavelet Transform and Timing Interval Features, IEEE Transactions on Biomedical Engineering vol. 53, Issue: 12, pp. 2507-2515.

L. Smith, A tutorial on Principal Components Analysis.

Akinori Ueno, et al. Capacitive sensing of electrocardiographic potential through cloth from the dorsal surface of the body in a supine position: a preliminary study. IEEE Transactions on Biomedical Engineering, vol. 54, No. 4, Apr. 2007, pp. 759-766.

K. Oweiss, A. Mason, Y. Suhail, A. Kamboh and K. Thomson, "Scalable Wavelet Transform VLSI Architecture for Real-Time Signal Processing in High-Density Intra-Cortical Implants", IEEE Trans. Circuits Syst. I, vol. 54, No. 6, pp. 1266-1278.

K. Todros and J. Tabrikian, "Blind Separation of Independent Sources Using Gaussian Mixture Model," IEEE Transactions on Signal Processing, vol. 55, No. 7, pp. 3645-3658 (Jul. 2007).

R. Sameni, M. Shamsollahi, C. Jutten and G. Glifford, "A Nonlinear Bayesian Filtering Framework for ECG Denoising," IEEE Transactions on Biomedical Engineering, vol. 54, No. 12, pp. 2172-2185 (2007).

X. Li, X. Yao, J. J Fox, and J. Jefferys, "Interaction Dynamics of Neuronal Oscillations Analysed Using Wavelet Transforms," Journal of Neuroscience Methods 160, pp. 178-185 (2007).

R Schimpf, Ch Antzelevitch, D Haghi, C Giustetto, A Pizzuti, F Gaita, Ch Veltmann, Ch Wolpert, and M Borggrefe. Electromechanical coupling in patients with the short QT syndrome: Further insights into the mechanoelectrical hypothesis of the U wave. Heart Rhythm. Feb. 2008; 5(2): 241-245.

Sarkar S, Ritscher D, Mehra R. A detector for a chronic implantable atrial tachyarrhythmia monitor. IEEE Trans Biomed Eng. Mar. 2008;55(3):1219-24.

M. Malik, K. Hnatkova, T. Novotny, G Schmidt Subject-specific profiles of QT/RR hysteresis. Am J Physiol Heart Circ Physiol 295:H2356-H2363, 2008.

Akturk, A. and Goldsman, N. (2008) "Electron transport and fullband electron phonon interactions in graphene" J. of Applied Physics 103.

S. Paredes, T. Rocha, P. de Carvalho, and J. Henriques, "Atrial Activity Detection through a Sparse Decomposition Technique," vol. 2, pp. 358-362, 2008 International Conference on BioMedical Engineering and Informatics, 2008.

R. Sameni, C. Jutten and M. Shamsollahi, "Multichannel Electrocardiogram Decomposition Using Periodic Component Analysis," IEEE Transactions on Biomedical Engineering, vol. 55, No. 8, pp. 1935-1940 (Aug. 2008).

O. Adeyemi, et. al., "QA interval as an indirect measure of cardiac contractility in the conscious telemeterised rat: Model optimisation and evaluation," Journal of Pharmacological and Toxicological Methods. 60, pp. 159-166 (2009).

H. Li, R. Li, F. Wang. Multiresolution Subband Blind Source Separation: Models and Methods. Journal of Computers, vol. 4, No. 7 (2009), 681-688.

Afonso, V.X.; Tompkins, W.J.; Detecting ventricular fibrillation. IEEE Engineering in Medicine and Biology Magazine, vol. 14, Issue: 2, pp. 152-159.

Dash S, Chon Kh, Lu S, Raeder EA. Automatic real time detection of atrial fibrillation. Ann Biomed Eng. Sep. 2009;37 (9):1701-9. Epub Jun. 17, 2009.

M. Hassan, J. Terrien, B. Karlsson, and C. Marque, "Spatial Analysis of Uterine EMG Signals: Evidence of Increased in Synchronization with Term," Conf Proc IEEE Eng Med Biol Soc, vol. 1, pp. 6296-6299 (Sep. 2009).

R. Yang, Y. Qin, C. Li, G. Zhu, Z. Lin Wang, "Converting Biomechanical Energy into Electricity by a Muscle-Movement-Driven Nanogenerator," Nano Letters, vol. 9, No. 3, pp. 1201-1205 (2009).

J. Piccini, et al, Predictors of sudden cardiac death change with time after myocardial infarction: results from the Valiant trial. European Heart Journal (2009).

J. Lipponen, M. Tarvainen, T. Laitinen, T. Lyyra-Laitinen, and P.A. Karjalainen, "Principal Component Regression Approach for Estimation of Ventricular Repolarization Characteristics," IEEE Trans Biomed Eng., vol. 57, No. 5, pp. 1062-1069 (2010).

S.Hadei, M. Iotfizad. A family of adaptive filter algorithms in noise cancellation for speech enhancement. International Journal of Computer and Electrical Engineering, vol. 2, No. 2, Apr. 2010. 1793-8163.

Allen, M., Tung, V., Kaner, R. (2010) " Honey Carbon: A Review of Graphene" Chem. Rev. 110:132-145.

Attila S. Farkas. et. al. Biomarkers and endogenous determinants of dofetilide-induced torsades de pointes in α1-adrenoceptor-stimulated, anaesthetized rabbits. British Journal of Pharmacology. vol. 161, Issue 7, pp. 1477-1495, Dec. 2010.

HJ van der Linde, B Van Deuren, Y Somers, B Loenders, R Thwart and DJ Gallacher, The Electro-Mechanical window: a risk marker for Torsade de Pointes in a canine model of drug induced arrhythmias, British Journal of Pharmacology (2010) 161 1444-1454.

Daubechies I., et al. Synchrosqueezed wavelet transforms: an empirical mode decomposition-like tool. Applied and Computational Harmonic Analysis, vol. 30, Issue 2, Mar. 2011, pp. 243-261.

M. Brockway and R Hamlin, "Evaluation of an algorithm for highly automated measurements of QT interval," Journal of Pharmacological and Toxicological Methods, vol. 64, pp. 16-24 (2011).

http://www.physionet.org/physiobank/database/#ecg.

http://www.physionet.org/physiobank/database/mitdb/.

J.-p. Martinez, et. al., "A wavelet-based ECG delineator: Evaluation on standard databases," IEEE transactions on biomedical engineering, vol. 51, No. 4, pp. 57 (2004).

Thomsen, M. B., Verduyn, S. C., Stengl, M., Beekman, J. D., de Pater, G., van Opstal, J., et al. (2004). Increased short-term variability of repolarization predicts d- sotalolinduced torsade de pointes in dogs. Circulation, 110, 2453-2459.

M. Alghoniemy and A. Tewfik, "Reduced Complexity Bounded Error Subset Selection," IEEE Int. Conf. Acoustics, Speech and Signal Processing (ICASSP), pp. 725-728 (Mar.. 2005).

K. Oweiss, A. Mason, Y. Suhail, A. Kamboh and K. Thomson, "A Scalable Wavelet Transform VLSI Architecture for Real-Time Signal Processing in High-Density Intra-Cortical Implants", IEEE Trans. Circuits Syst. I, vol. 54, No. 6, pp. 1266-1278 (Jun. 2007).

R. Sameni, C. Jutten and M. Shamsollahi, "Multichannel Electrocardiogram Decomposition Using Periodic Component Analysis," IEEE Transactions on Biomedical Engineering, vol. 55, No. 8, pp. 1935-1940.

Allen, M., Tung, V., Kaner, R. (2010) "Honey Carbon: A Review of Graphene" Chem. Rev. 110:132-145.

HJ van der Linde, B Van Deuren, Y Somers, B Loenders, R Thwart and DJ Gallacher, The Electro-Mechanical window: A risk marker for Torsade de Pointes in a canine model of drug induced arrhythmias, British Journal of Pharmacology (2010) 161 1444-1454

\* cited by examiner

ECG SENSING WITH NOISE FILTERING

RELATED PATENT DOCUMENTS

This patent document is a continuation-in-part under 35 U.S.C. §120 of U.S. patent application Ser. No. 13/293,632 filed on Nov. 10, 2011 (U.S. Pat. No. 8,543,195), which claims the benefit under 35 U.S.C. §119 of U.S. Provisional Patent Application Ser. No. 61/412,108 filed on Nov. 10, 2010; U.S. patent application Ser. No. 13/293,632 is further a continuation-in-part of U.S. patent application Ser. No. 12/938,995 (U.S. Pat. No. 8,632,465) filed on Nov. 3, 2010, and which claims the benefit of U.S. Provisional Patent Application Ser. No. 61/257,718 filed on Nov. 3, 2009, and of U.S. Provisional Patent Application Ser. No. 61/366,052 filed on Jul. 20, 2010, to all of which priority is claimed via 35 U.S.C. §120 for common subject matter; each of these patent documents is fully incorporated herein by reference.

FIELD OF INVENTION

Various aspects of the present invention relate to ECG sensing, and more particular aspects relate to an ECG sensing lead having an active electronic module that removes in-band noise from a sensed ECG signal.

BACKGROUND

In-band noise from EMG and other sources is an obstacle to the extraction of accurate, reliable, and repeatable information from ambulatory ECG recordings. This issue is prevalent in multiple applications where ambulatory monitoring is used including diagnosis and management of patients at risk of cardiac arrhythmias and preclinical and clinical evaluation of drug safety and effectiveness.

Ambulatory ECG monitoring devices often incorporate the ability to detect arrhythmic events and store the ECG strip containing the event for later communication to a computerized system for further review. ECG strips detected by the ambulatory monitoring device as containing an arrhythmia are communicated to a computerized system where the strips containing the events are subjected to further analysis and are evaluated to screen out inaccurate and erroneous information. Other ambulatory devices record the ECG continuously or at regular intervals, and the ECG is communicated to a computerized system where intervals are measured and events are detected. Whether the ECGs are analyzed within the ambulatory monitoring device, at a computerized system located in an office, laboratory, or center dedicated to ECG analysis, or a combination thereof, noise can render the ECGs uninterpretable or very difficult to interpret and cause analysis algorithms to produce large numbers of false positive events and errors in interval measurements, requiring manual over-read of the results. This increases labor costs and risks introducing human error, leading to inferior information. For preclinical and clinical drug safety studies, where intervals and arrhythmias are often documented during analysis, noise introduces variability that increases the sample size necessary to reach statistical significance and creates false positives and errors that require expensive manual over-read. These and other matters present challenges to ECG monitoring.

SUMMARY

Various aspects of the present invention are directed to devices, methods, and systems for removing in-band noise from ECG signals (denoising the ECG) sensed on or near the skin surface, prior to recording on an ambulatory monitoring device and in a manner that addresses challenges, including those discussed above.

An example embodiment is directed to an apparatus having two or more electrodes that sense an ECG signal, a denoising module communicatively coupled to the at least two electrodes, and a communication circuit. The denoising module receives the ECG signal, and includes circuitry that conditions and digitizes the ECG signal, as well as a computing circuit that processes said digitized ECG signal to denoise the ECG signal based upon a time-based distribution of subcomponents of the signal. The communications circuit generates a communication including the denoised ECG signal for access by a device remote from the communications circuit.

Another embodiment is directed to an apparatus comprising two or more electrodes that sense an ECG signal, digitizing circuitry that is communicatively coupled to the at least two electrodes and that generates a digitized ECG signal from the ECG signal sensed via the electrodes, and a computing circuit coupled to the digitizing circuitry. The computing circuit generates a denoised ECG signal from the digitized ECG signal, in which the denoised ECG signal has (relative to the digitized ECG signal) an improved signal-to-noise ratio of at least 15 dB as measured using the ANSI EC 57 standard, and a quality of signal reconstruction greater than 95%.

Another embodiment is directed to apparatus having two or more electrodes that sense an ECG signal, a wireless communication circuit, digitizing circuitry and a computing circuit coupled to the digitizing circuitry. The wireless communication circuit wirelessly communicates an ECG signal that corresponds to the sensed ECG signal, with a remote receiver. The digitizing circuitry generates a digitized ECG signal from the ECG signal sensed via the electrodes. The computing circuit generates a denoised ECG signal from the digitized ECG signal, in which the denoised ECG signal has (relative to the digitized ECG signal) an improved signal-to-noise ratio of at least 15 dB as measured using the ANSI EC 57 standard, and a quality of signal reconstruction greater than 95%.

According to another example embodiment, a denoising module for removing in-band noise of an ECG signal is incorporated into an ECG sensing lead. The complete lead includes at least two connectors located on the distal end of the lead that conductively connect to surface electrodes on or near the skin of a patient, a first lead body conductively connecting the signal sensed by the surface electrodes to the module, the denoising module, and a second lead body conductively connecting the module to a connector on the proximal end of the lead. The connector on the proximal end of the lead plugs into a mating connector on the ambulatory monitoring device. This active ECG sensing lead with integral denoising module provides a denoised ECG signal with output levels compatible with ambulatory monitoring devices and can be used as a replacement for standard passive ECG leads that are used to connect ECG sensing electrodes to an ambulatory monitor.

In one aspect of the present invention, connecting snaps that mate with the skin surface electrodes are connected to the module using wires. The sensed ECG signals are conditioned and digitized and are then processed by a logic circuit or computer processor configured to execute an algorithm for removing in-band noise. The denoised ECG signals are then converted back to low-level analog signals compatible with ambulatory monitoring devices. A second lead body conductively connects the denoised ECG signal from the module to a connector that plugs into the ambulatory monitoring device. In another aspect of this invention, the second lead body is eliminated and the module contains an integral connector that plugs into the ambulatory monitoring device for conductively communicating the denoised ECG signal to the ambulatory monitoring device.

In one aspect of the present invention, an algorithm for removing in-band noise employs adaptive filtering. In another aspect of this invention, the algorithm for removing in-band noise employs a decomposition and thresholding technique. In another aspect of the present invention, the algorithm for removing in-band noise employs multi-domain signal processing techniques. In yet another aspect of the present invention, the ECG signal is comprised of two or more channels and the algorithm for removing in-band noise employs principal component analysis.

BRIEF DESCRIPTION OF THE DRAWINGS

The invention may be more completely understood in consideration of the following detailed description of various embodiments of the invention in connection with accompanying drawings, in which.

Figure 1:
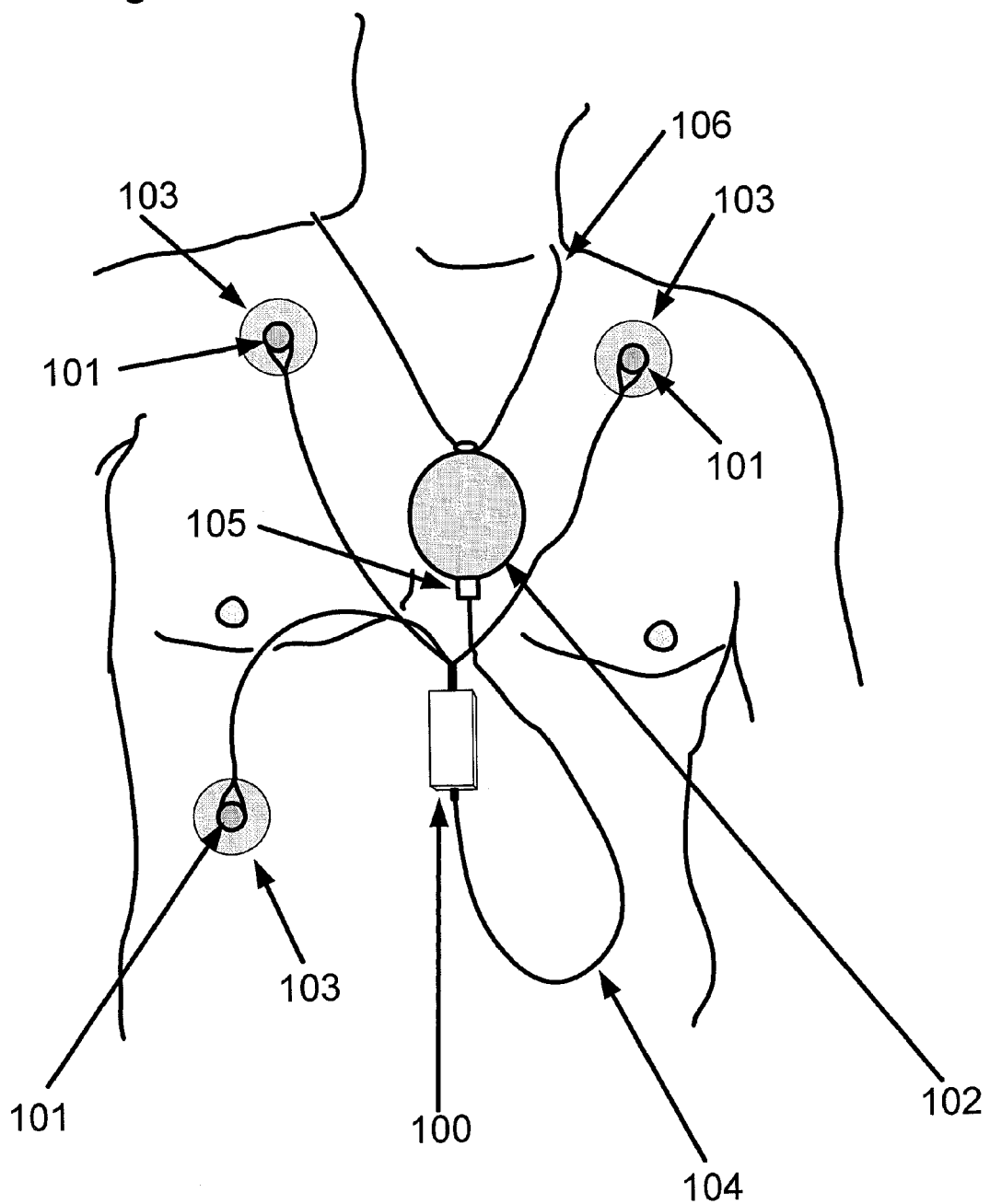
FIG. 1 shows a subject wearing an ambulatory monitoring device employing an ECG lead with integral denoising module, consistent with an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the invention including aspects defined in the claims.

DETAILED DESCRIPTION

Various example embodiments of the present invention relate to an active lead for sensing an ECG at or near the surface of the body of a subject, removing in-band noise from the sensed ECG, and providing a denoised output signal similar in amplitude to the sensed ECG signal. The active ECG sensing lead with denoising capability, which is the subject invention, can be used with a large installed base of ambulatory monitoring devices already in existence and can be substituted for commonly used passive sensing leads. While the present invention is not necessarily limited to such applications, various aspects of the invention may be appreciated through a discussion of examples using this context.

Certain embodiments of the present invention describe the use of Multi-Domain Filtering (MDF). The term MDF is used herein to refer to embodiments that use Multi-Domain Signal Processing (MDSP) to denoise an ECG signal. Various embodiments of the present invention are directed to denoising ECG signals sensed at the surface of the body of a human being or animal. In the context of this invention, denoising refers to removing in-band noise, or noise present within the bandwidth of the ECG signal.

In the following discussion, reference is made to cited references listed in a numbered order near the end of this document, which are fully incorporated herein by reference. These references may assist in providing general information regarding a variety of fields that may relate to one or more embodiments of the present invention, and further may provide specific information regarding the application of one or more such embodiments.

An example embodiment is directed to an apparatus having two or more electrodes that sense an ECG signal, a denoising module and a communication circuit. These components may, for example, be integrated in a common unit and/or with one of the electrodes being remote, such as for adhesion to a patient's skin. Aspects of the denoising module facilitate denoising that is sufficient for identifying ECG signal components, which can mitigate unnecessary communication of undesirable signals and enjoy lower processing and power overhead. The denoising module is communicatively coupled to the at least two electrodes, and receives the ECG signal sensed by the sensing electrodes. The denoising module also includes circuitry that conditions and digitizes the ECG signal, and a computing circuit that processes said digitized ECG signal to denoise the ECG signal based upon a time-based distribution of subcomponents of the signal. The communications circuit generates a communication including the denoised ECG signal for access by a device remote from the communications circuit.

Another embodiment is directed to an apparatus having two or more electrodes that sense an ECG signal, digitizing circuitry that is communicatively coupled to the at least two electrodes and that generates a digitized ECG signal from the ECG signal sensed via the electrodes, and a computing circuit coupled to the digitizing circuitry. The computing circuit generates a denoised ECG signal from the digitized ECG signal, in which the denoised ECG signal has (relative to the digitized ECG signal) an improved signal-to-noise ratio of at least 15 dB as measured using the ANSI EC 57 standard, and a quality of signal reconstruction greater than 95%. Such a computing circuit may, for example, be a portable computer circuit such as a mobile telephone that receives the ECG signal sensed by the sensing electrodes. In some implementations, the quality of signal reconstruction (QSR) may is defined as $$QSR = 100\% * \left(1 - \frac{\sum_i (x_{cl}^j - x_{den}^j)^2}{\sum_i (x_{cl}^j)^2}\right),$$

in which $x_{cl}$ is the digitized ECG signal and $x_{den}$ is the denoised ECG signal.

In some implementations, the denoised ECG signal is generated from a digitized ECG signal that has a signal-to-noise ratio of 0 dB and that includes a substantially noise-free ECG with white noise added as prescribed in the ANSI EC 57 standard. In this context, substantially noise-free refers to a signal with less noise than desired signal, and in some instances, a signal having a signal-to-noise ratio of greater than 30 dB according to the ANSI EC 57 standard.

The denoising is carried out in a variety of manners to suit particular embodiments. In some embodiments, the computing circuit decomposes the digitized ECG signal from a first domain into subcomponents in a second domain that is different than the first domain, and generates the denoised ECG signal by selecting and combining ones of the subcomponents based upon a time-based distribution thereof. In certain embodiments, the subcomponents are combined by first identifying target subcomponents of the input signal that are associated with a desired ECG signal based upon the time-based distribution of the subcomponents. A denoised ECG signal is then reconstructed in the first domain from at least two of the identified target subcomponents.

In some embodiments, one or more apparatuses as discussed above are implemented for coupling to a patient, such as by adhesion of the apparatus to a patient's skin. The denoising characteristics facilitate the use of compact and lightweight circuitry that is amenable to such implementation. In a particular such embodiment, the apparatus includes an adhesive substrate that adheres to a patient, with the electrodes being coupled to the substrate and operate with the substrate to adhere to the patient and sense the ECG signal. The digitizing circuitry and computing circuit are also coupled to the substrate between the electrodes. In a more particular embodiment, the apparatus also includes a wireless communication circuit coupled to the substrate, and which wirelessly communicates the denoised ECG signal with a remote transceiver. A battery can be implemented for powering the digitizing circuitry, computing circuit and wireless communication circuit, with the substrate supporting the battery while adhered to the patient. In certain implementations, a housing connected to the substrate encloses the digitizing circuitry, computing circuit, wireless communication circuit and battery, with the substrate supporting the housing while adhered to the patient and the housing being disposed between the first and second electrodes. In some embodiments, the computing circuit and digitizing circuitry sample each ECG signal at 300 Hz or less, and the computing circuit reduces in-band noise of the digitized ECG signal using an average power consumption that is less than 500 micro-Watts per ECG signal.

According to an example embodiment, and referring to FIG. 1, skin electrodes 103 are positioned on the chest of a body surface of a subject to be monitored, sense an ECG signal and are electrically connected to conductive wires via snaps 101. In this embodiment, there are three skin electrodes used to provide two ECG signals (two channels). In an alternate embodiment, two electrodes are placed on the skin of the patient to provide a single channel ECG signal. In yet other alternate embodiments, additional skin electrodes and corresponding conductive wires can be added to provide additional ECG signal channels. The conductive wires extend from each snap to a point of convergence where they consolidate into a lead body that connects to denoising module 100. Denoising module 100 outputs a low-level analog signal of an amplitude similar to the ECG signal sensed by skin electrodes 103. The output signal is conductively communicated by lead body 104 to connector 105 that plugs into ambulatory monitoring device 102 worn by the subject. In this embodiment, ambulatory monitoring device 102 is suspended from lanyard 106 worn around the neck of the monitored subject. In alternate embodiments, skin electrodes may be adhesive backed electrodes such as 3M (St. Paul, Minn.) Red Dot electrodes. Alternately, the skin electrodes may be dry electrodes in direct contact with surface tissue and incorporated into an elastic strap worn around the subject's thorax, such as from Polar Electro (Kempele, Finland). Alternately, the skin electrodes may be dry electrodes positioned or woven into the fabric of a garment worn by the subject and designed to be in contact with the subject's skin such as is available from Textronic, Inc. (Wilmington, Del.). In one embodiment, a garment has multiple ECG electrodes incorporated into the fabric, each electrically connected to the denoising module. The denoising module could be incorporated into a small pouch in the fabric with a lead body extending from the denoising module for connection to an ambulatory monitoring device. In some embodiments the denoising module can be wirelessly connected to a monitoring device such as a heart rate monitor. Alternately, the skin electrodes may be capacitive sensing electrodes such as those described in [1]. In an embodiment that employs capacitive sensing electrodes, additional signal conditioning circuitry can be used to convert the capacitance modulated signal to a voltage representing the ECG signal for input to denoising module 100.

Figure 2:
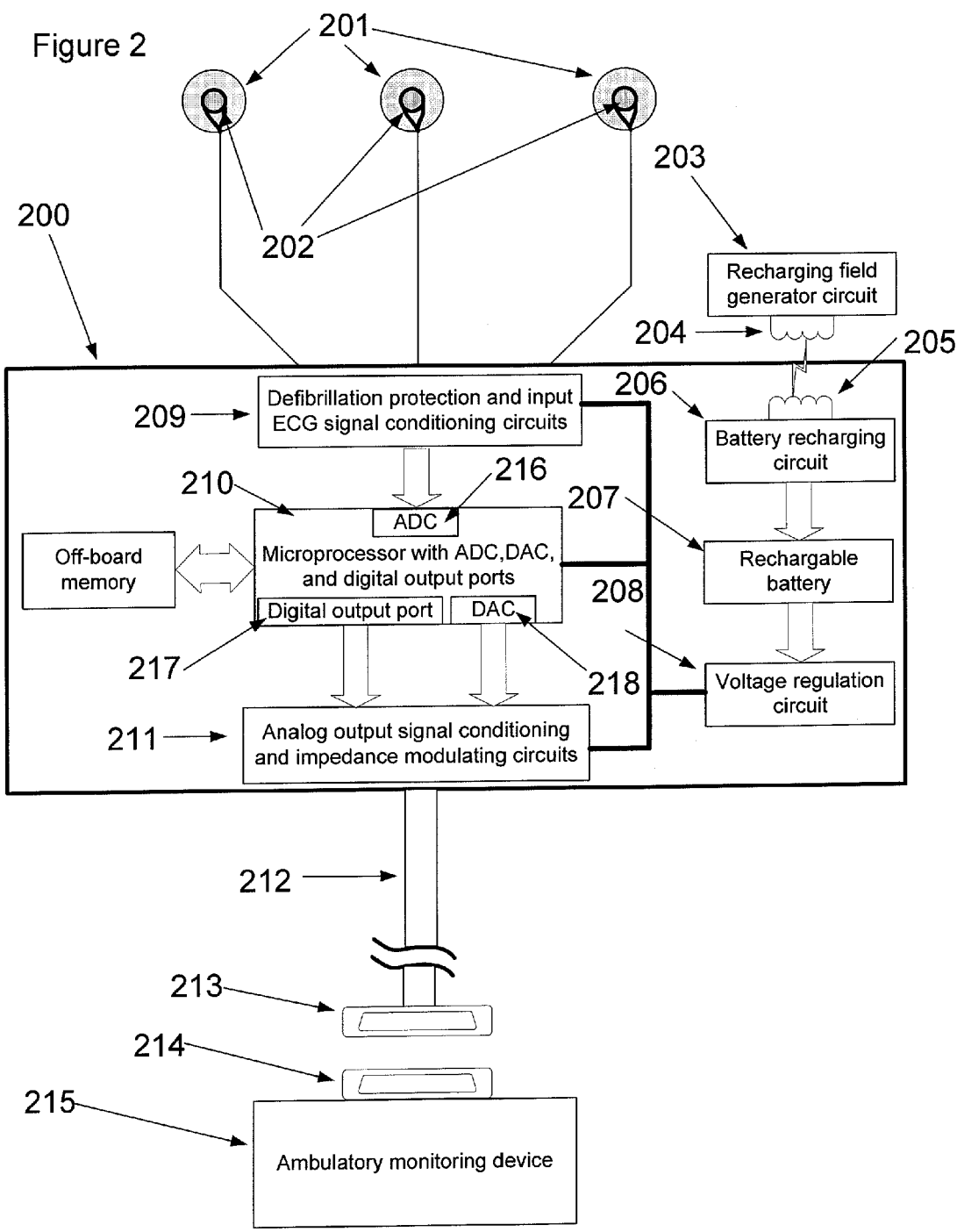
FIG. 2 shows a block diagram of the sensing lead and functional components of a denoising module; consistent with an example embodiment of the present invention.

Referring to FIG. 2, skin electrodes 201 are conductively connected to denoising module 200 by snaps 202 attached to lead wires. Signal conditioning and defibrillation protection circuits 209 protect the electronics from damage in the event the patient is defibrillated as well as amplify the sensed ECG signal. In some embodiments, the circuits 209 may include an anti-aliasing filter that removes energy from the signal outside the band of the frequencies contained in the ECG signal.

In one embodiment, the device shown in FIG. 2 is implemented for monitoring a human ECG, and the amplifier circuits in 209 increase the amplitude of the sensed ECG by a factor of 1,000 from 2.5 mV to 2.5 Volts peak-to-peak and will pass frequencies from 0.05 Hz to 100 Hz. In another embodiment, the device shown in FIG. 2 is used to monitor other species, and the gain and filter settings are different than those used for a human ECG.

The conditioned ECG signal is digitized using an analog-to-digital converter (ADC) 216 in microprocessor chip 210. In one embodiment, chip 210 is a Texas Instruments (Dallas, Tex.) MSP-430 microcontroller. A 16-bit RISC processor executes algorithms to remove in-band noise. The denoised ECG signal is converted to an analog signal via digital-to-analog converter (DAC) 218 incorporated in chip 210. In some embodiments, ADC 216 and DAC 218 may be separate from microprocessor chip 210. The analog output signal is conditioned in circuit 211 to provide filtering and any signal level adjustments necessary to provide compatibility with ambulatory monitoring device 215. The analog output signal is conductively communicated to connector 213 via lead body 212. Connector 213 mates with connector 214 of ambulatory monitoring device 215.

In one embodiment of the present invention, and referring to FIG. 2, an automatic amplitude control (AAC) function can be implemented in chip 210. The AAC attempts to maintain relatively constant QRS complex amplitude. This approach is useful, for example, when used with ambulatory monitoring devices 215 having limitations in QRS detection algorithm where changes in amplitude can be detrimental to performance.

In some embodiments, ambulatory monitoring device 215 is configured to evaluate the integrity of the conductive coupling between skin electrodes 201 and the skin of the subject. This is performed by circuits within device 215 that measure impedance between skin electrodes 201. When an impedance level indicative of poor coupling is detected, device 215 may notify the subject of a problem via an alarm. It is therefore useful for this active sensing lead to detect poor quality ECG signals and modulate an impedance measured by device 215 when poor quality ECG signals are detected. In some embodiments, an algorithm implemented by microprocessor 210 monitors the quality of the signal sensed by skin electrodes 201. If skin electrodes 201 are not making adequate contact with the skin or the skin has not been properly prepared, or the electrodes have not been properly positioned, the signal quality may be poor. When the microprocessor 210 detects that signal quality is unacceptable, it sends a logic level signal to circuit 211 via digital output port 217 to modulate an impedance that is evaluated by ambulatory monitoring device 215. The impedance can be modulated, for example, by switching a high-value resistor in series with an analog signal line carrying the denoised ECG signal to ambulatory monitoring device 215. The switch used to insert the series resistor is activated by a logic-level signal provided from chip 210 via digital output port 217 when the algorithm has detected a poor quality signal.

In some embodiments, denoising module 200 is powered by a primary cell battery that can be replaced via an access in the housing of module. In some embodiments, denoising module 200 is contained in a sealed housing. This may be useful in preventing ingress of moisture that may negatively impact the reliability of the denoising module. For embodiments where the housing of denoising module 200 is sealed, it is useful to use a rechargeable battery such as lithium ion battery or thin film battery. In this embodiment, battery 207 is recharged by recharging circuit 206. Circuit 206 includes inductor 205 to receive a varying magnetic field induced by inductor 204. Circuit 206 processes the alternating voltage produced by inductor 205 and converts it to a direct current suitable for charging battery 207. Recharging field generator circuit 203 provides a varying voltage to inductor 204 to produce the varying magnetic field. It is anticipated that inductor 204 will be placed near or directly adjacent to the location of inductor 205 in order to facilitate a faster charge time for battery 207. In some embodiments, it is anticipated that the charge time for battery 207 will be a few hours and that charging will be required every 1 to 4 weeks. Power regulation circuits 208 regulate the voltage to circuits 209 and 211 and to microprocessor 210. In another embodiment a supercapacitor capable of storing a large amount of charge is used to power the denoising module 200 (e.g., as an alternative to the battery 207).

Figure 3:
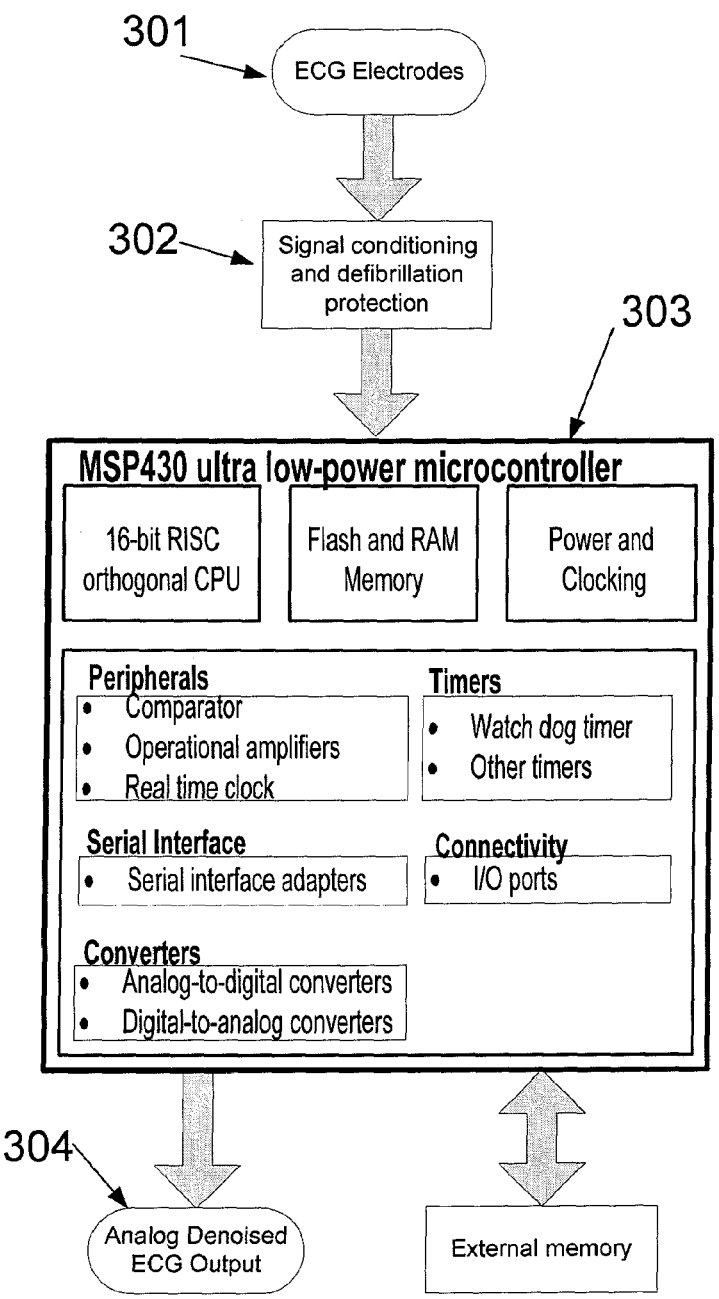
FIG. 3 shows a block diagram of portions of a denoising module, consistent with an example embodiment of the present invention.
Figure 4:
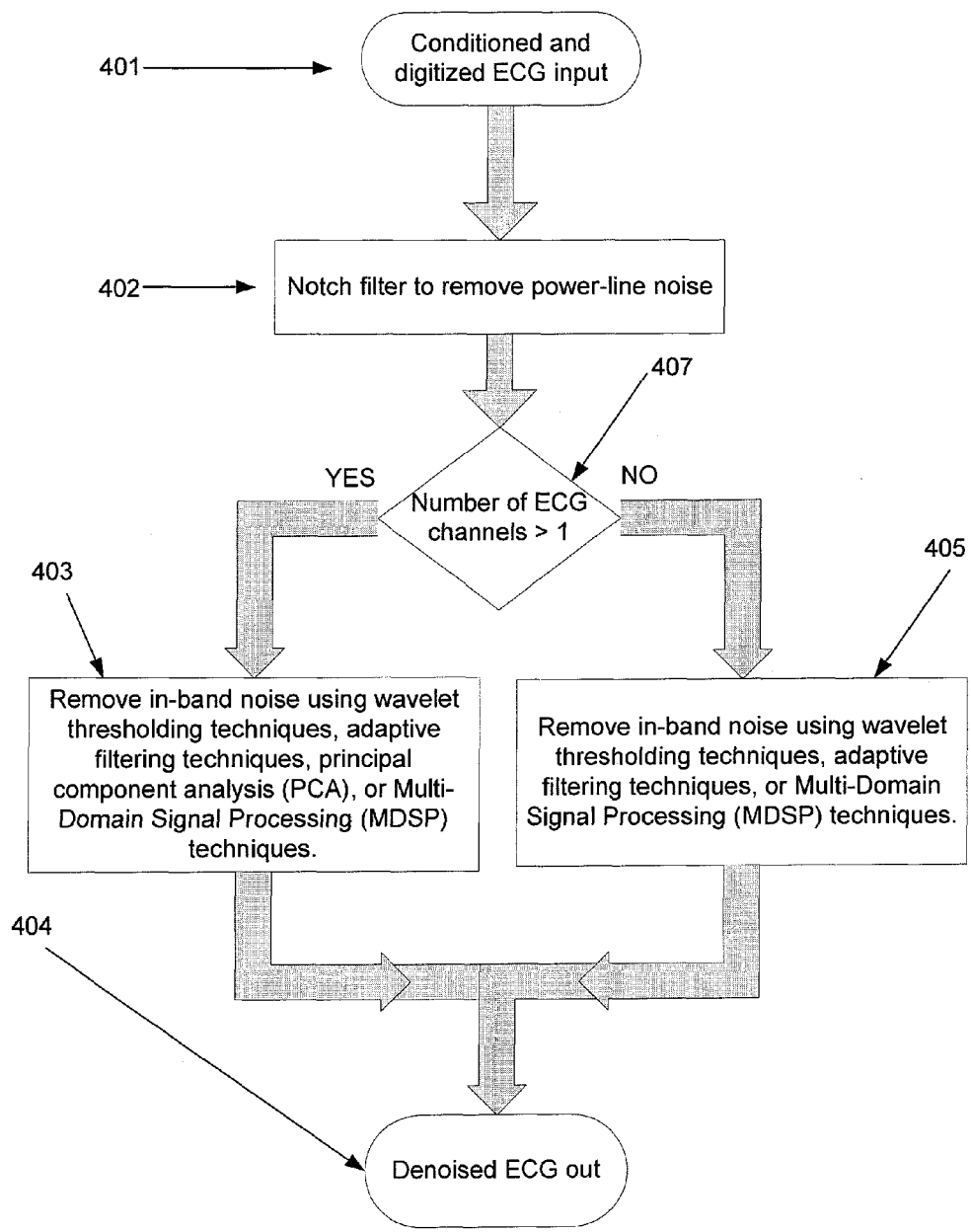
FIG. 4 shows a high-level signal flow diagram of a denoising module, consistent with an example embodiment of the present invention.

Referring to FIG. 3, the sensed ECG signal from electrodes 301 is conditioned by circuits 302 as described herein. The microprocessor 303 executes an algorithm to remove noise from the input ECG signal. Each input channel of the conditioned ECG signal is digitized by an analog-to-digital converter incorporated on the Texas Instruments (Dallas, Tex.) MSP-430 microcontroller chip. In some embodiments, and referring to FIG. 4, the digitized signal 401 is first processed to remove power line noise (e.g. either 60 Hz or 50 Hz, depending upon power line frequency used in individual country) using notch filter 402. In one embodiment, notch filter 402 is implemented using infinite impulse response (IIR) filtering techniques. In other embodiments, power line noise is removed by the denoising process executed by microprocessor 303 in process 403 or 405. In one embodiment, referring to FIG. 4, the possible algorithms used for denoising depends upon the number of channels in the ECG signal. If there is only one channel, denoising is directed by decision point 407 to process 405 and is accomplished using one of adaptive filtering, decomposition and thresholding, and Multi-Domain Signal Processing (MDSP). If there is more than one channel, denoising is directed by decision point 407 to process 403 and is accomplished using one of principal component analysis, adaptive filtering, decomposition and thresholding, and Multi-Domain Signal Processing (MDSP). Following denoising the signal is converted to an analog signal using a digital-to-analog converter at 404.

Figure 5:
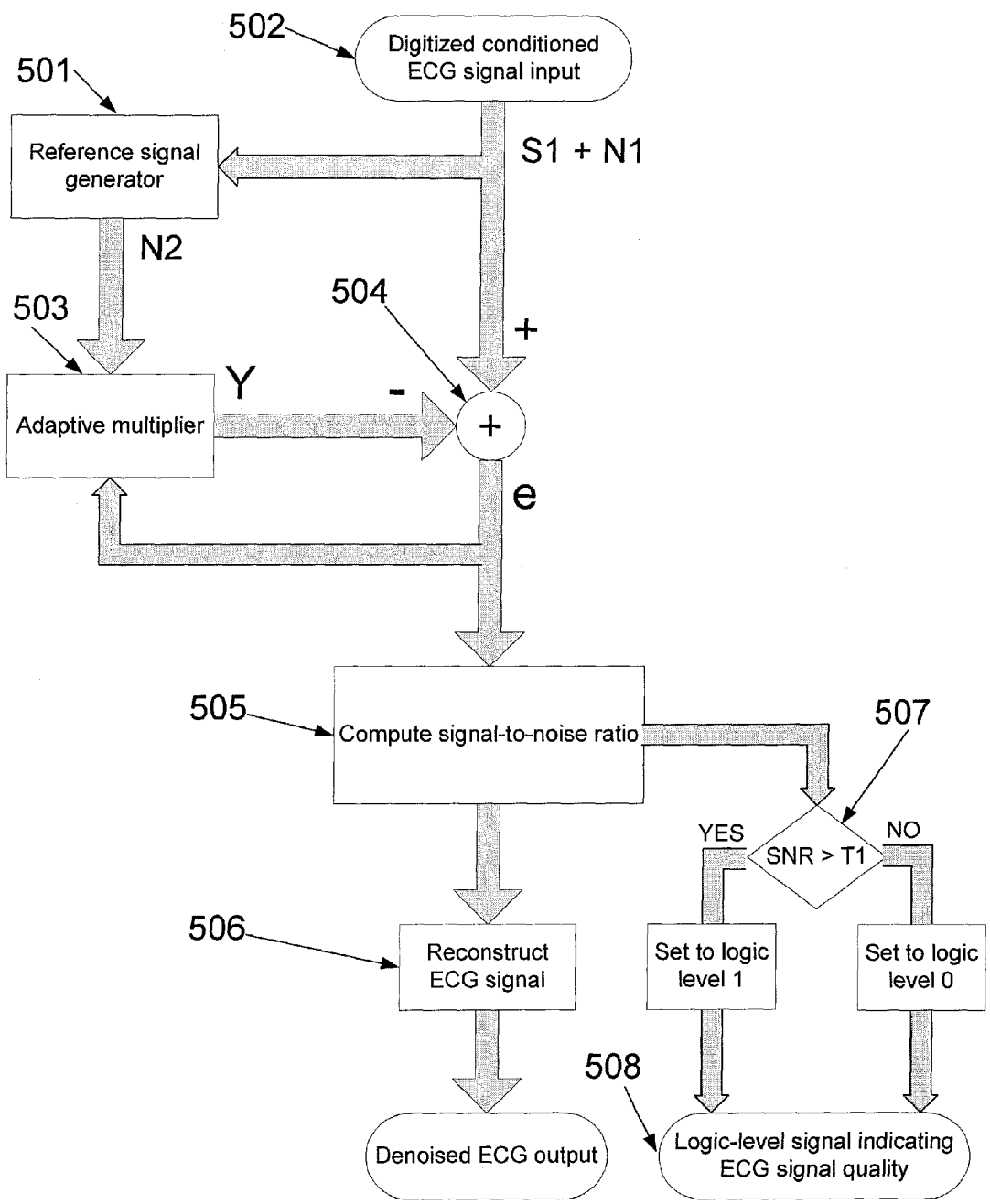
FIG. 5 shows a signal flow diagram of an adaptive filtering denoising algorithm as implemented in a denoising module, consistent with an example embodiment of the present invention.

In one embodiment, and referring to FIG. 5, the digitized ECG signal 502 is denoised using adaptive filtering techniques [4, 5]. The input ECG signal 502 is composed of a desired signal S1 that is corrupted with noise N1. Signal 502 is preprocessed to extract a noise reference signal N2 using reference generator 501. Noise reference signal N2 is correlated with noise signal N1. The adaptive filter algorithm estimates and updates the parameters of adaptive multiplier 503 to minimize the least squared error between the output Y of adaptive multiplier 503 and input signal 502. Summation node 504 computes the difference between the input signal 502 and the output of adaptive multiplier 503. The resulting difference signal e is an estimate of the desired signal S1 when the least squared error between the output Y of 503 and input signal 502 is minimized.

In another embodiment reference signal N2 is acquired independently by a skin electrode, separate from the skin electrodes that produced input signal 502, rather than generating a reference signal from the input signal 502. When the reference signal N2 is a sensed ECG signal S1 is extracted by minimizing mean square error between input signal 502 and the reference signal N2. Examples of techniques that minimize mean square error include least-mean squares, normalized least mean squares, recursive least squares, adaptive recurrent filter, fast affine projection, and fast Euclidean direction [6].

In the process 505, the output signal Y of adaptive multiplier 503 is used as an estimate of noise for computing noise power and the denoised signal e output from summation node 504 is used to compute signal power. The SNR is then computed in process 505 according to formula $$SNR_{db} = 10\log_{10}\left(\frac{P_{signal}}{P_{noise}}\right) \quad (1)$$

where $P_{signal}$ and $P_{noise}$ are respective signal and noise energy. SNR is used to evaluate input signal quality. For example, if a skin electrode is not properly attached, the quality will be poor and would result in a low SNR value. SNR is evaluated relative to a predetermined threshold Ti in decision point 507. A logic-level 0 signal is generated in process 508 if SNR<Ti to signal to circuit 211 of FIG. 2 that a resistor should be inserted into the analog signal line in communication with ambulatory monitoring device 215. Insertion of the resistor effectively increases source impedance in the ECG signal line to ambulatory monitoring device 215, thereby emulating the situation of an increase in source impedance that would occur if a skin electrode of a passive lead were to have come loose. If the ambulatory monitoring device incorporates a mechanism based upon source impedance to signal to the subject that a lead has come loose, it will generate an alarm signal to that effect, as described herein. ECG signals are reconstructed at 506.

Figure 6:
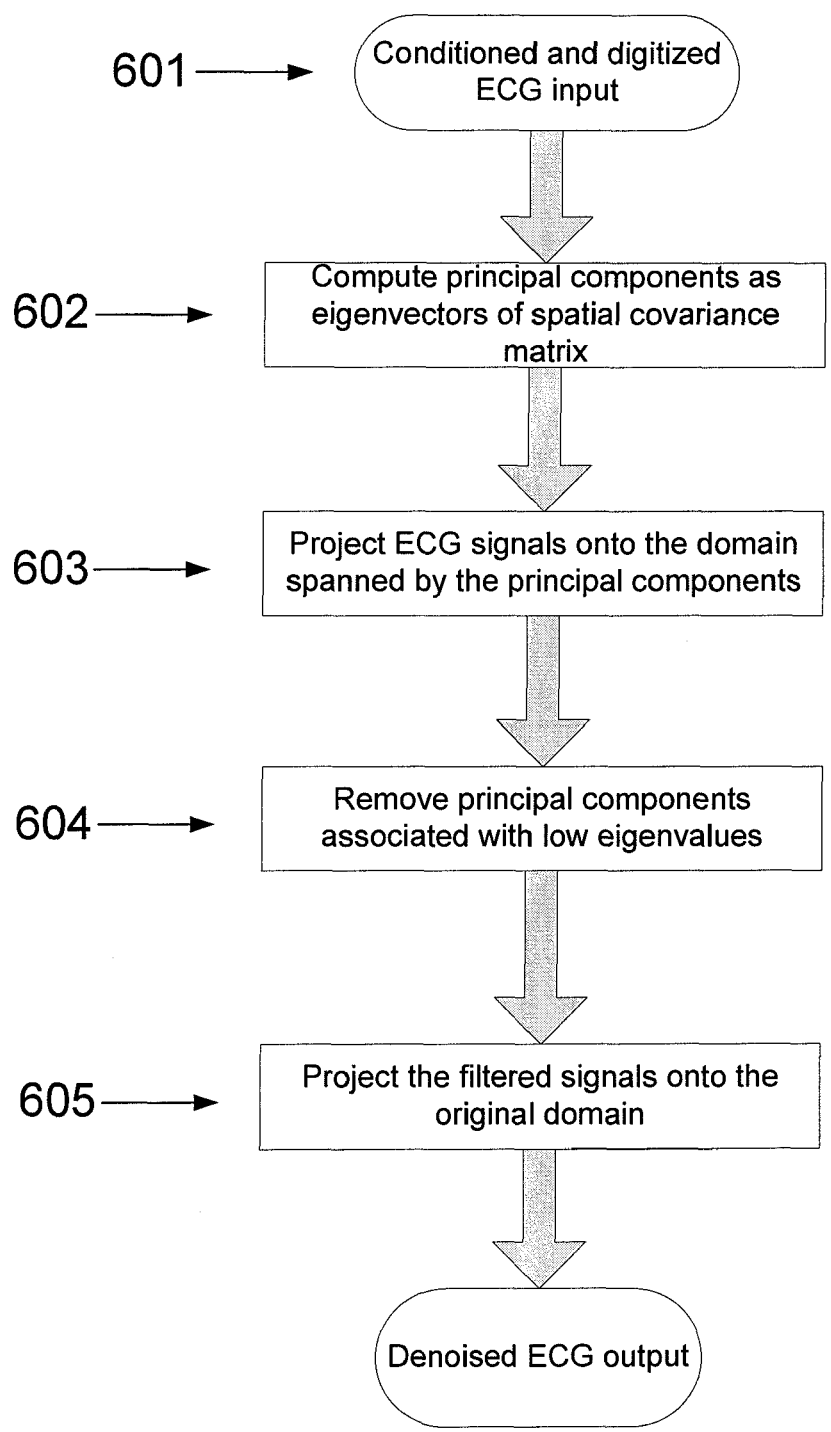
FIG. 6 shows a signal flow diagram of a principal component analysis denoising algorithm as implemented in a denoising module, consistent with an example embodiment of the present invention.

In another embodiment, and referring to FIG. 6, the digitized ECG signal 601 is denoised using principal component analysis (PCA). In this embodiment the multi-channel ECG signal is projected onto the domain of its principal components [7]. The principal components are computed in process 602 by performing eigenvalue or singular value decomposition of the spatial covariance matrix computed from ECG signals. The projection of ECG signals onto the domain of their principal components is performed in process 603 by multiplying the ECG signals by the extracted unitary matrix of eigenvectors or singular vectors. This linear projection results in new signals that are uncorrelated with normalized variance. Geometrically, the projection involves rotation and scaling of the data in order to orthogonalize signal components. Among the orthogonalized components, the ones with low signal power are often associated with noise and can be removed to achieve denoising. The data are filtered by zeroing the principal components associated with smaller eigenvalues in process 604. In one embodiment the filtered data can be projected back onto the original domain at 605 using the unitary matrix of eigenvectors to retain original signal morphology.

In one embodiment PCA is performed in combination with independent component analysis technique (ICA) [8] for denoising. In this embodiment, PCA is performed as a preliminary step to decorrelate the signals prior to applying ICA for noise removal. In various embodiments involving the use of an ICA technique for denoising the signal, noise sources are separated by achieving their mutual independence. In one embodiment the problem of maximizing independence of ECG recording from contaminating noise is found as a solution of an optimization problem that maximizes independence between the signal sources. For example, ICA techniques can use either higher-order statistics of signal components [9, 10] or information-theoretic criteria to maximize independence. Information-theoretic criteria that can be applied include maximization of negentropy or its approximation [11], minimization of mutual information [11], maximum likelihood estimation [12, 13], maximum a posteriori probability [14], or expectation-maximization of Gaussian mixture models of sources [15]. These solutions can be approximated via efficient numerical methods, such as FastICA [16] and JADE [11] algorithms.

In some embodiments, it is useful to compute signal-to-noise ratio (SNR) of the input signal 601 when denoising using PCA. The parameters required in Formula 1, $P_{signal}$ and $P_{noise}$, can be computed as a byproduct of the PCA denoising process. $P_{signal}$ can be estimated as the sum of the eigenvalues of the retained principal components in process 604. Likewise, $P_{noise}$ can be estimated as the sum of the eigenvalues of the principal components removed in process 604.

Figure 7:
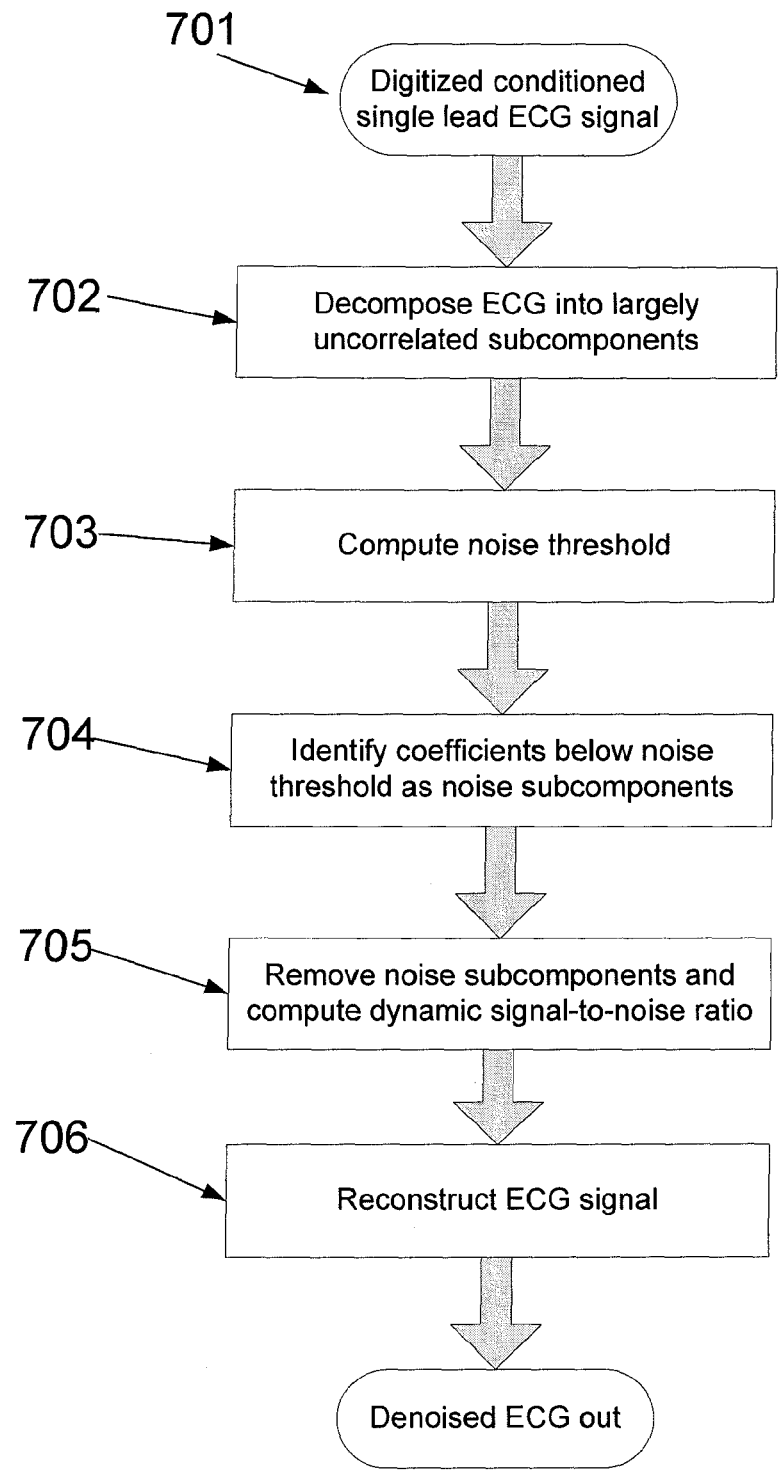
FIG. 7 shows a signal flow diagram of the decomposition and thresholding denoising algorithm as implemented in a denoising module, consistent with an example embodiment of the present invention.

In another embodiment, and referring to FIG. 7, the digitized ECG signal 701 is denoised using a signal decomposition and thresholding technique (SDTT), in accordance with another example embodiment of the present invention. In process 702 input signal 701 is decomposed into subcomponents in a second domain of larger dimension than the first domain. The dimension of the first domain is defined by the number of observed, or captured, signal channels. The dimension of the second domain is defined by the number of channels multiplied by the number of subcomponents in each channel. Decomposition step 702 is performed using one of a variety of transforms that result in a small signal reconstruction error. Such transforms may include, for example, a discrete cosine transform [17], a wavelet related transform [19], a Karhunen-Loeve transform [21], a Fourier transform [18], a Gabor transform [20], or a filter bank [19]. In one embodiment, denoising is facilitated by a decomposition whereby signal energy is concentrated in a small number of large subcomponent coefficients, while noise is spread out across either many decomposition levels or decomposition levels corresponding to higher frequency and is represented by small coefficients. In process 705, the signal quality is enhanced by discarding subcomponents below a threshold computed in process 703. The energy in the discarded subcomponents is used to estimate noise energy in process 705. Signal energy, for computing SNR in process 705 is estimated using the residual subcomponents representing the denoised ECG signal. SNR is computed from noise energy and signal energy estimates as described herein. In some implementations, instead of discarding subcomponents below a threshold, those subcomponents above a threshold (the residual subcomponents above) can be positively identified and used to estimate the signal energy, with the remaining energy being noise. Techniques similar to soft or hard thresholding [23] can be used to remove this noise in process 704. Examples of a threshold selection rule used to compute the noise threshold in process 703 include adaptive threshold selection using the principle of Stein's Unbiased Risk Estimate and fixed threshold based on signal statistics such as SD*sqrt(2*log(length (X)), where SD is standard deviation and X is a vector of subcomponents [22]. The residual subcomponents are combined in process 706 to reconstruct an ECG signal using the inverse of the transform used for signal decomposition in process 702.

Figure 8:
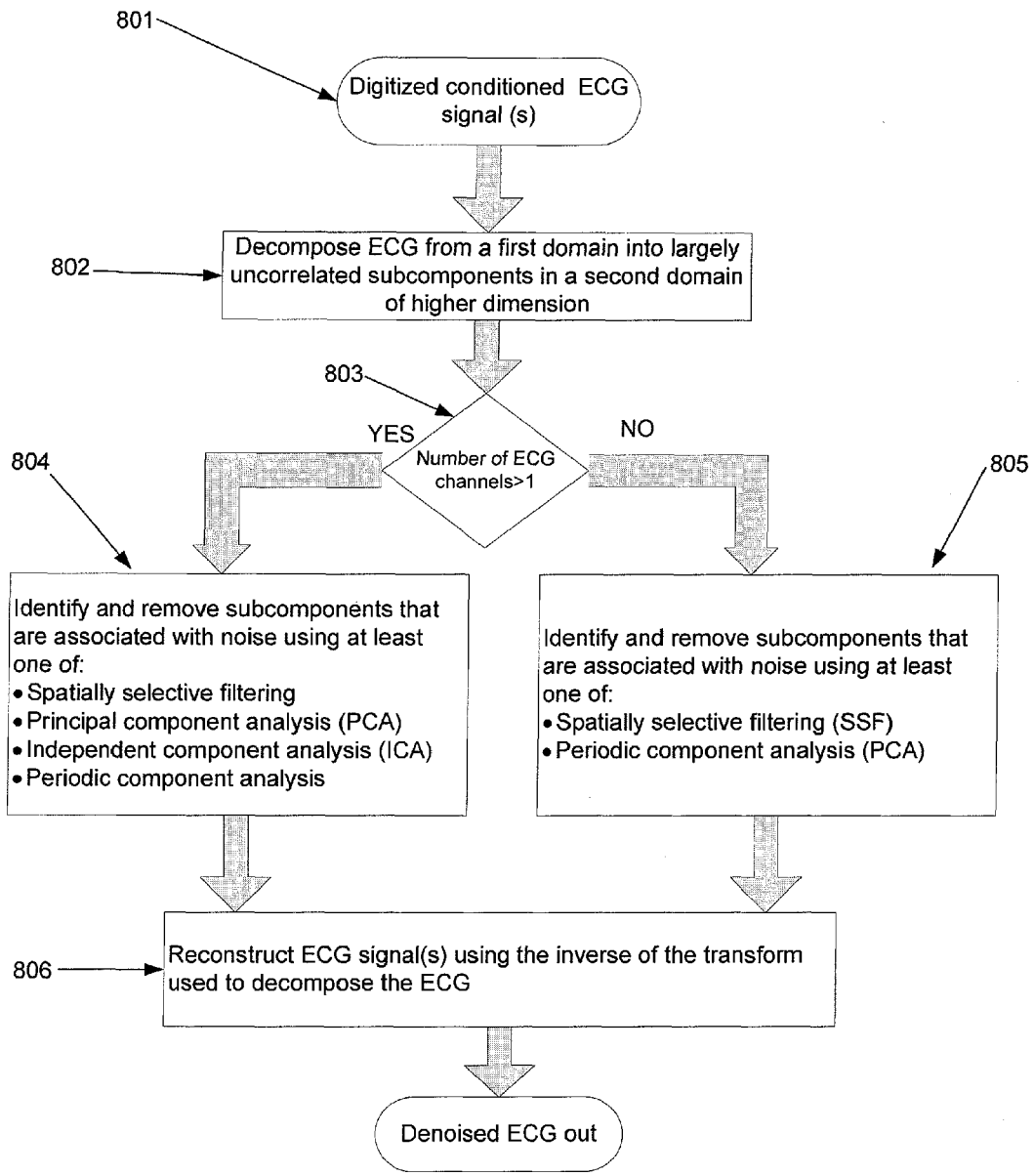
FIG. 8 shows a signal flow diagram of a Multi-Domain Signal Processing (MDSP) denoising algorithm as implemented in the denoising module, consistent with an example embodiment of the present invention.

Referring to FIG. 8, the digitized ECG is denoised using an MDSP embodiment. Input signal 801 is decomposed in process 802 from a first domain into largely uncorrelated subcomponents in a second domain of higher dimension. Decomposition in process 802 is accomplished using one of a discrete cosine transform, a Karhunen-Loeve transform, a Fourier transform, a Gabor transform, and a filter bank. In another embodiment, decomposition is accomplished using a wavelet-related transform and the decomposition levels correspond to wavelet scales. In another embodiment, decomposition is achieved by representing the observed signals as a linear combination of basis functions. Signal decomposition embodiments and the use of subcomponents derived from the decomposition for denoising (removal of at least some of the in-band noise contained in the signal), extraction of information from the signal, and evaluation of the accuracy of extracted information is referred to as Multi-Domain Signal Processing (MDSP) by way of example, in the discussion herein. Use of MDSP techniques for removal of in-band noise from a signal is referred to as Multi-Domain Filtering (MDF).

The dimension of the first domain is defined by the number of ECG channels. The dimension of the second domain is defined by the number of channels multiplied by the number of subcomponents in each channel. Following decomposition, signal flow is directed to either process 804 or 805 by decision point 803, depending upon the number of channels in the signal. If the ECG signal has only one channel, signal flow is directed to process 805, where either spatially selective filtering (SSF) [24, 28, 29] or periodic component analysis [25, 26] are used alone or in combination to identify subcomponents that contain more noise energy than signal energy. If the ECG signal has more than one channel, signal flow is directed to process 804, where either spatially selective filtering, principal component analysis [27], independent component analysis, or periodic component analysis are used either alone or in combination to identify subcomponents that contain more noise energy than signal energy. A subcomponent that contains more noise than signal energy is said to be associated with noise. Conversely, a subcomponent that contains more signal energy than noise energy is said to be associated with a signal.

In some embodiments, processes 804 and 805 result in separation of subcomponents into two groups, one associated with noise and the other associated with the ECG signal. Determining whether a subcomponent is associated with noise or ECG signal within a targeted interval of time is accomplished by using one or more of principal component analysis (PCA), independent component analysis (ICA), periodic component analysis (RCA) and spatially selective filtering (SSF). PCA and ICA are applicable to multi-lead ECG, while RCA and SSF can be applied to either multi-lead or single-lead ECG.

The PCA technique [7,27] employed in processes 804 and 805 uses subcomponent covariance information to orthogonalize subcomponents. The orthogonalized subcomponents with low signal power are often associated with noise and can be removed to achieve denoising. PCA can be used as a preliminary step prior to applying an ICA technique. The ICA technique further separates signal and noise sources [8] as a solution of an optimization problem that maximizes independence between them. The RCA technique computes and jointly diagonalizes covariance and autocorrelation matrices of subcomponents to separate them based on their periodicity or quasi-periodicity [25, 26]. The RCA technique extracts most periodic subcomponents corresponding to ECG rhythm and, since noise is not generally periodic, it is left behind.

SSF techniques [24, 28, 29] employed in processes 804 and 805 detect one or more signal-related features (e.g., QRS complex) and pass them across the subcomponents while blocking features inherent to noise. The technique relies on the differences of noise and signal distributions across decomposition levels. In one embodiment, spatially selective filtering is facilitated by a decomposition whereby signal energy is concentrated in a small number of large subcomponent coefficients while noise is spread out across many decomposition levels and is represented by small coefficients. Techniques similar to wavelet thresholding [23] can be used to remove this noise.

In another embodiment of process 804 and 805, a spatially selective filtering approach exploits the fact that most noise subcomponents are confined to decomposition levels that represent high frequencies. In this embodiment the locations of signal features are identified by examining subcomponents corresponding to lower frequency. For example, a QRS wave location can be identified as high amplitude changes in peaks and valleys that occur simultaneously across multiple subcomponents associated with lower frequencies. To avoid signal distortion, the subcomponents associated with high frequency are preserved within the time window surrounding the identified peaks and valleys, and are zeroed at other times. By zeroing out the subcomponents or time segments within subcomponents associated with noise, and reconstructing the ECG signal using those subcomponents associated with the ECG signal, the in-band noise level in the ECG is reduced, or "denoised", to create a denoised ECG.

The subcomponents identified as associated with noise in processes 804 and 805 are removed and the residual subcomponents are used to reconstruct a denoised ECG signal for each ECG channel in process 806 using the inverse of the transform used to decompose the ECG in process 802. In some implementations, instead of removing subcomponents that are associated with noise, subcomponents associated with signal energy are identified (the residual subcomponents above) and used to estimate the signal energy, with the remaining energy being noise.

In some embodiments involving an MDSP-based approach, a signal-to-noise ratio (dSNR) is computed as the ratio of the energies in signal and noise subcomponents. In one embodiment, referring to FIG. 8, following separation of subcomponents into two groups, as described herein in processes 804 and 805, the power in each of the groups, $P_{signal}$ and $P_{noise}$, is independently computed and used to compute SNR as per formula 1.

Figure 9:
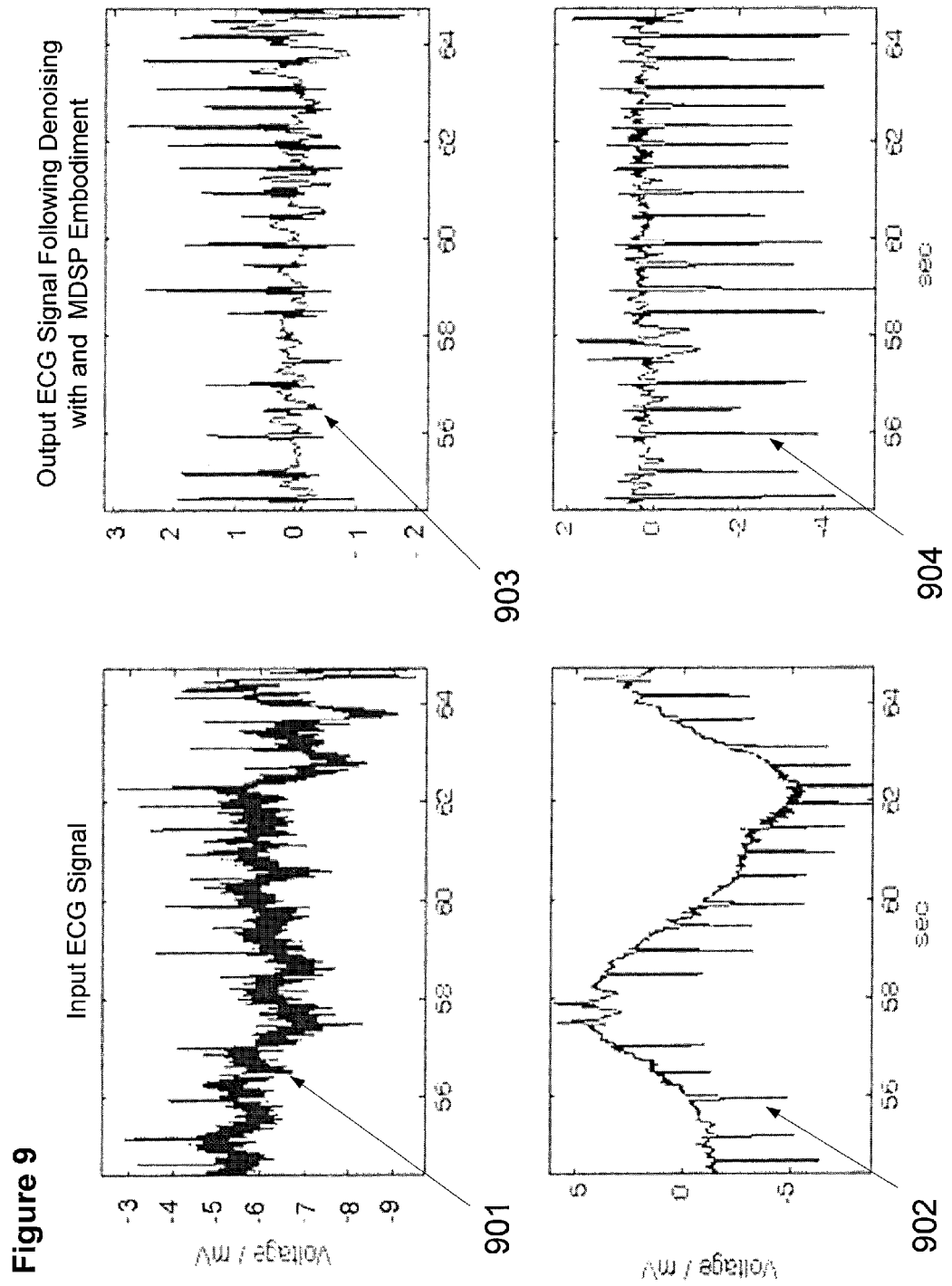
FIG. 9 shows an example of a two-lead ECG signal that has been denoised using an MDSP embodiment, consistent with an example embodiment of the present invention.

Referring to FIG. 9, an example of a two channel ECG signal denoised by an MDSP embodiment is provided. Input signals 901 and 902 are recordings of a human ambulatory ECG and were obtained from the MIT-BIH database. Output ECG traces 903 and 904 are shown for each channel. The improvement in SNR in this example is approximately 8 dB and noise amplitude is reduced by about 85% with no noticeable distortion.

Figure 10:
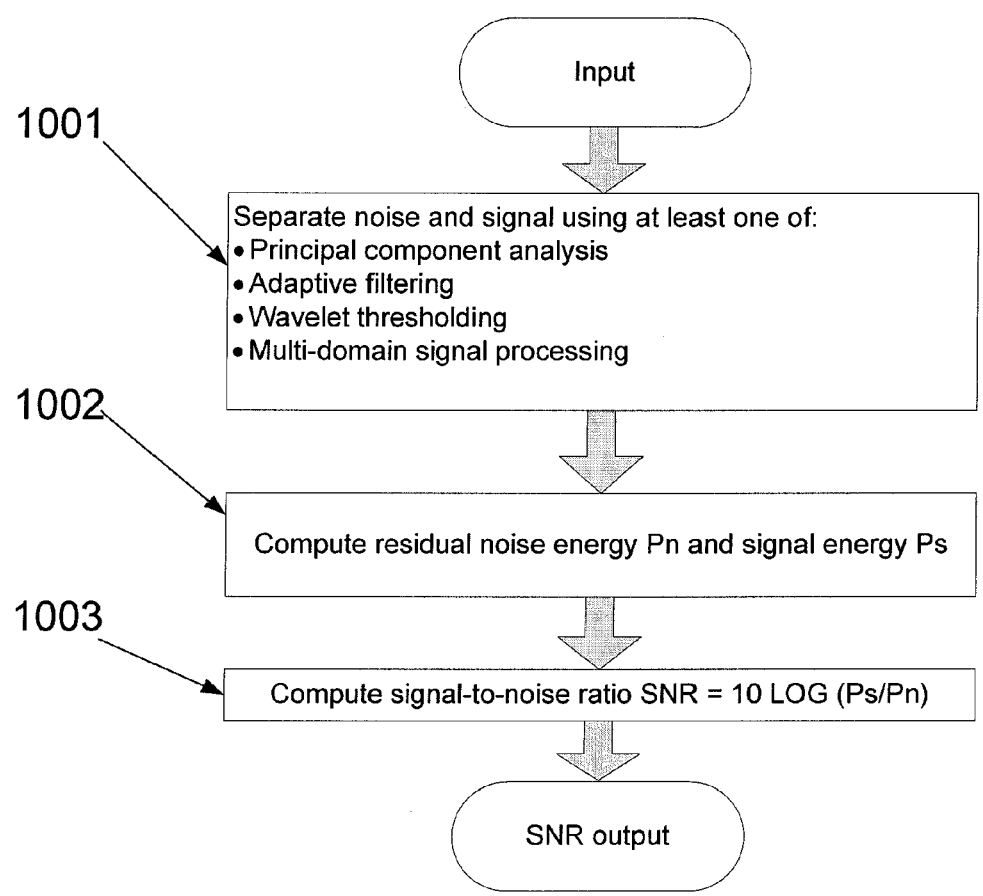
FIG. 10 shows a signal flow diagram for computing a signal-to-noise ratio for an ECG signal, consistent with an example embodiment of the present invention.

In some embodiments, and referring to FIG. 10, signal-to-noise ratio is computed for evaluating signal quality. As described herein, a measure of signal quality can be useful to change the effective source impedance of the ECG signal communicated to the ambulatory monitoring device when the device is configured to detect unusually high source impedance as an indicator that an ECG sensing electrode is in poor contact with the skin. In process 1001, signal and noise are separated. Some embodiments for separating signal and noise, described herein, include adaptive filtering, decomposition and thresholding, principal component analysis, and MDSP denoising embodiments. In process 1002, separated noise and signal are used to estimate signal energy and noise energy. SNR is computed in process 1003, as described herein. The approach used in process 1001 to separate signal and noise would typically match the process technique used for denoising, as the signal and noise values can be computed as a byproduct of the denoising process. Hence the technique used in 1001 will depend upon the method of denoising.

Various embodiments as described herein can be used in connection with ambulatory monitoring devices. For instance, devices as discussed herein can be used as a substitute for existing passive ECG leads used with ambulatory monitoring devices, such as Holter monitors, event recorders, and Mobile Cardiac Outpatient Telemetry devices. Such devices may be used, for example, to improve performance of these devices in one or more of a variety of manners.

In some embodiments, denoising module 200 includes a wireless communication link to communicate the denoised ECG to a location away from the body of the subject from which the ECG is obtained.

The various computing components, circuits and signal processing methods described herein can be implemented using a variety of devices and methods. For example, computing, logic or processing circuits can be implemented using one or more of: discrete logic circuitry, fully-programmable and semi-programmable circuits such as PLAs (programmable logic arrays), specialized processors or general purpose processors that are specially programmed. Combinations of these and other circuit components are also possible and within the scope of various embodiments, including those discussed above. For example, the various components and processes shown in the figures can be implemented in a variety of circuit-based forms, such as through the use of data processing circuit modules. Such systems are exemplified by implementation in high-speed programmable computer/processor circuits, or in combination with discrete and or semi-programmable circuitry (e.g., as Field-Programmable Gate Arrays, Programmable Logic Devices/Arrays).

Figure 11:
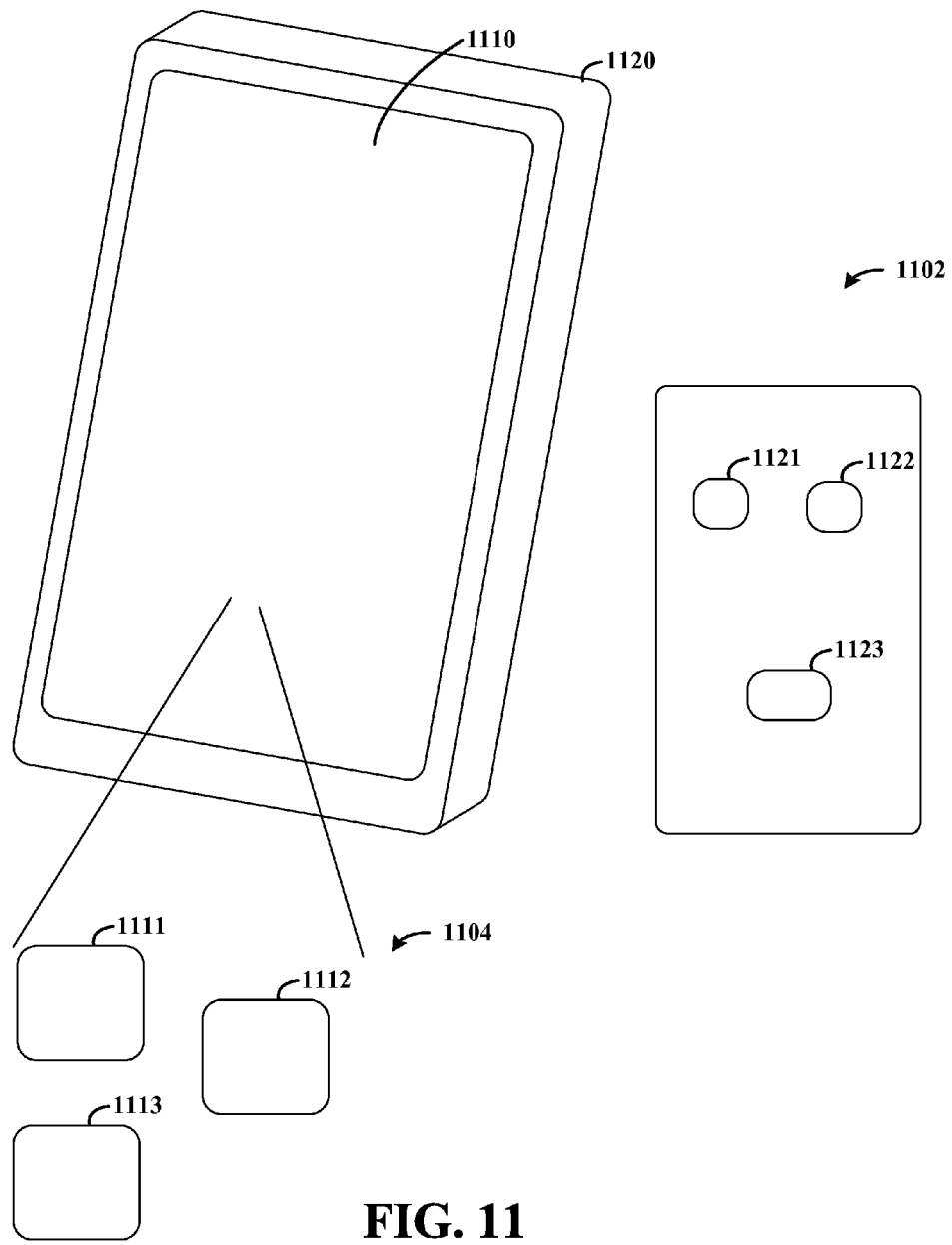
FIG. 11 shows an apparatus including a portable computing circuit and a chassis for sensing ECG signals, in accordance with another example embodiment.

FIG. 11 shows an apparatus including a portable computing circuit 1110 and a chassis 1120 for sensing ECG signals, in accordance with another example embodiment. The chassis 1120 includes ECG electrodes 1121 and 1122, as well as wireless communication circuitry 1123, which are shown on an inset back-side view 1102 by way of example. The electrodes 1121/1122 sense an ECG signal from a patient, and the wireless communication circuitry 1123 wirelessly communicates a wireless signal corresponding to the sensed ECG signal (e.g., via sound, or radio frequency signals). The portable computing circuit 1100 (e.g., a mobile telephone) includes wireless communication circuitry 1111 that receives the wireless signal, digitizing circuitry 1112 that digitizes the wireless signal, and a computing circuit 1113 that generates a denoised ECG signal from the digitized wireless signal, as shown at inset 1104. In some embodiments, computing circuit 1110 and chassis 1120 are operable for coupling to one another, such as by snapping the computing circuit 1110 into the chassis 1120. In some implementations, the wireless communication circuits each have at least one of a speaker and a microphone that communicate the ECG signal via sound waves.

Another embodiment, is directed to an ECG device having an electrode assembly that senses heart-related signals upon contact with a user's skin, and that converts the sensed heart-related signals to ECG electrical signals wherein the electrode assembly is positioned on an outer surface of a smartphone protective case. Such a device may, for example, be implemented with the apparatus shown in FIG. 1, with the following referring to FIG. 1 by way of example. A converter assembly (e.g., 1123) includes an audio transmitter for outputting frequency modulated ultrasonic signals, and is integrated with and electrically connected to the electrodes for receiving the ECG electrical signals generated thereby, and output ECG sound signals through the audio transmitter to a microphone in a computing device within range of the audio transmitter (e.g., 1110). For instance, the converter assembly may output the ECG signals as an ultrasonic FM sound signal, with the audio transmitter outputting the ultrasonic FM sound signal to a microphone in a computing device within range of the audio transmitter. This output may, for example, be detectable by a microphone in a smartphone (e.g., 1110) when the smartphone is positioned within the smartphone protective case (e.g., 1120).

Such an approach, with digitizing and computing circuitry as discussed herein, can be implemented to achieve an improved signal-to-noise ratio of at least 15 dB as measured using the ANSI EC 57 standard, and a quality of signal reconstruction greater than 95%. For instance, the digitizing circuitry may be implemented to receive the ECG electrical signals via the ultrasonic FM sound signal. The converter assembly may include the digitizing circuitry and the computing circuit, and may output the ECG sound signals based upon the denoised ECG For general information regarding apparatuses that may be implemented for sensing signals, and for specific information regarding such apparatuses as may be implemented above, such as via using one or more denoising approaches as discussed herein, reference may be made to U.S. Pat. No. 8,301,232 and U.S. Pat. No. 8,460,189, which are fully incorporated herein by reference.

REFERENCES CITED

For general information regarding a variety of fields that may relate to one or more embodiments of the present invention, and for specific information regarding the application of one or more such embodiments, reference may be made to the following documents, which are fully incorporated herein by reference.

Various ones of these references are further cited above via corresponding numerals, and may be implemented as such.
1. Akinori Ueno, et al. Capacitive sensing of electrocardiographic potential through cloth from the dorsal surface of the body in a supine position: a preliminary study. IEEE Transactions on Biomedical Engineering, vol. 54, no. 4, April 2007, pp 759-766
4. N. V. Thakor and Y. Zhu, "Applications of adaptive filtering to ECG analysis: noise Cancellation and arrhythmia detection," IEEE Trans. Biomedical Engineering, Vol. 38, No. 8, pp. 785-794, August 1991.
5. B. Widrow, et al., "Adaptive noise cancelling: principles and applications," IEEE Proc., Vol. 63, No. 12, pp. 1692-1716, December 1975.
6. S. Hadei, M. lotfizad. A family of adaptive filter algorithms in noise cancellation for speech enhancement. International Journal of Computer and Electrical Engineering, Vol. 2, No. 2, April 2010. 1793-8163
7. L. Smith. A tutorial on Principal Components Analysis, http://users.ecs.soton.ac.uk/hbr03r/pa037042.pdf
8. P. Comon, "Independent component analysis, a new concept?," Signal Process. Special Issue on Higher Order Statistics, vol. 36, no. 3, pp. 287-314, 1994.
9. J.-F. Cardoso, "High-order contrasts for independent component analysis," Neural Comput., vol. 11, no. 1, pp. 157-192, 1999.
10. Blaschke, T.; Wiskott, L.; CuBICA: independent component analysis by simultaneous third- and fourth-order cumulant diagonalization IEEE Transactions on Signal Processing, Volume 52, Issue 5, May 2004 Page(s):1250-1256
11. Hyvärinen, A. New approximations of differential entropy for independent component analysis and projection pursuit. In *Advances in Neural Information Processing Systems*, volume 10, pages 273-279.MIT Press.
12. Bell, A. and Sejnowski, T. An information-maximization approach to blind separation and blind deconvolution, Neural Computation, 7:1129-1159.
13. Cardoso, J.-F. Infomax and maximum likelihood for source separation. *IEEE Letters on Signal Processing*, 1997, 4, 112-114.
14. M. Zibulevsky, B. Pearlmutter, Blind source separation by sparse decomposition in a signal dictionary, Neural Computation 2001, v 13, pp 863-882.
15. Todros, K.; Tabrikian, J.; Blind Separation of Independent Sources Using Gaussian Mixture Model IEEE Transactions on Signal Processing Volume 55, Issue 7, Part 2, July 2007 Page(s):3645-3658
16. Hyvärinen, A. Fast and robust fixed-point algorithms for independent component analysis. IEEE Transactions on Neural Networks, 10(3):626-634.
17. K. R. Rao and P. Yip, Discrete Cosine Transform: Algorithms, Advantages, Applications San Diego, Calif.: Academic, 1990.

18. Mallat, S. G., and Zhang, Z., Matching Pursuits with Time-Frequency Dictionaries, IEEE TSP(41), No. 12, December 1993, pp. 3397-3415.
19. Vaidyanathan. Multi-rate Systems and Filter Banks, Prentice Hall, 1993
20. J. Woods. Subband Coding, Kluwer Academic Press, 1990.
21. K. S. Ball, L. Sirovich, L. R. Keefe. Dynamical eigenfunction decomposition of turbulent channel flow. International Journal for Numerical Methods in Fluids Volume 12, Issue 6, Date: 5 Apr. 1991, Pages: 585-604
22. Donoho, D. L., I. M. Johnstone (1994), "Ideal spatial adaptation by wavelet shrinkage," Biometrika, vol 81, pp. 425-455.
23. Donoho, D. L. (1995), "De-noising by soft-thresholding," IEEE Trans. on Inf. Theory, 41,3, pp. 613-627.
24. Xu, Yansun, et al. Wavelet transform domain filters: a spatially selective noise filtration technique, IEEE transactions on image processing 1994, vol. 3, no 6, pp. 747-758
25. L. K. Saul and J. B. Allen, "Periodic component analysis: An eigenvalue method for representing periodic structure in speech." in NIPS, [Online]. 2000, pp. 807-813. Available: http://www.cs.cmu.edu/Groups/NIPS/00papers-pub-on-web/SaulAllen.pdf
26. R Sameni, et. al. Multichannel electrocardiogram decomposition using periodic component analysis. IEEE Transactions on Biomedical Engineering, 2008 vol 55, no 8 pp 1935-1940
27. Aminghafari, M.; Cheze, N.; Poggi, J-M. (2006), "Multivariate de-noising using wavelets and principal component analysis," *Computational Statistics & Data Analysis*, 50, pp. 2381-2398
28. Mallat, S. G., Hwang, W. L., Singularity Detection and Processing with Wavelets, IEEE Transactions on Information Technology (38), 1991, pp. 617-643.
29. Pan Q., Zhang L. Dai G., et al. Two denoising methods by wavelet transform. IEEE Trans. on SP., 1999, 47(12): 3401-3406

Based upon the above discussion and illustrations, those skilled in the art will readily recognize that various modifications and changes may be made to the present invention without strictly following the exemplary embodiments and applications illustrated and described herein. For example, various aspects are directed to signal processing such as denoising using one or more approaches as described in one or more of the priority documents referenced above and incorporated herein. One such aspect involves the denoising of an ECG signal using one or more approaches described in connection with multi-domain signal processing as described in these documents. Such modifications and changes may include, for example, incorporating one or more aspects described in the above references and/or applying one or more embodiments thereto, or combining embodiments. These and other modifications do not depart from the true spirit and scope of the present invention, including that set forth in the following claims.

What is claimed is:
1. An apparatus comprising:
   at least two electrodes configured and arranged to sense an ECG signal;
   digitizing circuitry communicatively coupled to the at least two electrodes and configured and arranged to generate a digitized ECG signal from the ECG signal sensed via the electrodes; and
   a computing circuit coupled to the digitizing circuitry and configured and arranged to generate a denoised ECG signal from the digitized ECG signal, the denoised ECG signal having, relative to the digitized ECG signal,
      an improved signal-to-noise ratio of at least 15 dB as measured using the ANSI EC 57 standard, and
      a quality of signal reconstruction greater than 95%.
2. The apparatus of claim 1, wherein the computing circuit is configured and arranged to generate the denoised ECG signal from a digitized ECG signal that has a signal-to-noise ratio of 0 dB and that includes a substantially noise-free ECG with white noise added as prescribed in the ANSI EC 57 standard.
3. The apparatus of claim 2, wherein the substantially noise-free ECG is an ECG having a signal-to-noise ratio of greater than 30 dB according to the ANSI EC 57 standard.
4. The apparatus of claim 1, wherein the computing circuit is configured and arranged to
   decompose the digitized ECG signal from a first domain into subcomponents in a second domain that is different than the first domain, and
   generate the denoised ECG signal by selecting and combining ones of the subcomponents based upon a time-based distribution of the subcomponents.
5. The apparatus of claim 4, wherein the computing circuit is configured and arranged to select and combine ones of the subcomponents by
   identifying target subcomponents of the digitized ECG signal that are associated with a desired ECG signal based upon the time-based distribution of the subcomponents, and
   reconstructing a denoised ECG signal in the first domain from at least two of the identified target subcomponents.
6. The apparatus of claim 1, wherein the computing circuit is a portable computer.
7. The apparatus of claim 1, wherein the computing circuit is a mobile telephone configured and arranged to receive the ECG signal sensed by the electrodes.
8. The apparatus of claim 1, further including an adhesive substrate configured and arranged to adhere to a patient, and wherein
   the electrodes are coupled to the substrate and configured and arranged with the substrate to adhere to a patient and sense the ECG signal, and
   the digitizing circuitry and computing circuit are coupled to the substrate between the electrodes.
9. The apparatus of claim 8, further including a wireless communication circuit configured and arranged to wirelessly communicate the denoised ECG signal with a remote transceiver.
10. The apparatus of claim 9, further including a battery coupled to the substrate and configured and arranged to power the digitizing circuitry, computing circuit and wireless communication circuit, the substrate being configured and arranged to support the battery while adhered to the patient.
11. The apparatus of claim 10, further including a housing that encloses the digitizing circuitry, computing circuit, wireless communication circuit and battery, the housing being connected to the substrate and the substrate being configured and arranged to support the housing while adhered to the patient, the housing being disposed between the electrodes.
12. The apparatus of claim 10, wherein the computing circuit and digitizing circuitry are configured and arranged to sample each ECG signal at 300 Hz or less, and the computing circuit is configured and arranged to reduce in-band noise of the digitized ECG signal using an average power consumption that is less than 500 micro-Watts per ECG signal.
13. The apparatus of claim 1, wherein the quality of signal reconstruction (QSR) is defined as

$$QSR = 100\% * \left(1 - \frac{\sum_i (x_{cl}^i - x_{den}^i)^2}{\sum_i (x_{cl}^i)^2}\right),$$

wherein $x_{cl}$ is the digitized ECG signal and $x_{den}$ is the denoised ECG signal.

14. An apparatus comprising:
at least two electrodes configured and arranged to sense an ECG signal;
a wireless communication circuit configured and arranged to wirelessly communicate an ECG signal, corresponding to the sensed ECG signal, with a remote receiver;
digitizing circuitry configured and arranged to generate a digitized ECG signal from the ECG signal sensed via the electrodes; and
a computing circuit coupled to the digitizing circuitry and configured and arranged to generate a denoised ECG signal from the digitized ECG signal, the denoised ECG signal having, relative to the digitized ECG signal,
an improved signal-to-noise ratio of at least 15 dB as measured using the ANSI EC 57 standard, and
a quality of signal reconstruction greater than 95%.

15. The apparatus of claim 14,
wherein at least one of the electrodes and the wireless communication circuit are coupled to a common substrate that is configured and arranged with the electrodes to sense the ECG signal, and
further including a portable device including the digitizing circuitry, the computing circuit and a second wireless communication circuit configured and arranged to receive the wirelessly-communicated ECG signal, the digitizing circuitry being configured and arranged to generate the digitized ECG signal from the wirelessly-communicated ECG signal.

16. The apparatus of claim 15, wherein the wireless communication circuits are configured and arranged with at least one of a speaker and a microphone to communicate the ECG signal via sound waves.

17. The apparatus of claim 16, wherein the electrodes and the wireless communication circuit are integrated in a chassis configured and arranged to attach to the portable device and to generate sound waves, the portable device including microphone configured and arranged to receive the generated sound waves when attached to the chassis, and the second wireless communication circuit being configured and arranged with the microphone to receive the ECG signal communicated via the sound waves and to provide the received ECG signal to the digitizing circuitry.

18. An ECG device comprising:
an electrode assembly configured to sense heart-related signals upon contact with a user's skin, and to convert the sensed heart-related signals to ECG electrical signals wherein the electrode assembly is positioned on an outer surface of a smartphone protective case; and
a converter assembly including an audio transmitter for outputting frequency modulated ultrasonic signals, the converter assembly integrated with, and electrically connected to the electrode assembly and configured to receive the ECG electrical signals generated by the electrode assembly and output ECG sound signals through the audio transmitter to a microphone in a computing device within range of the audio transmitter, wherein the converter assembly is further configured to output the ECG signals as an ultrasonic FM sound signal, wherein the audio transmitter is configured to output the ultrasonic FM sound signal to a microphone in a computing device within range of the audio transmitter, wherein the output from the audio transmitter is detectable by a microphone in a smartphone when the smartphone is positioned within the smartphone protective case;
digitizing circuitry configured and arranged to generate a digitized ECG signal based on the ECG electrical signals generated by the electrode assembly; and
a computing circuit coupled to the digitizing circuitry and configured and arranged to generate a denoised ECG signal from the digitized ECG signal, the denoised ECG signal having, relative to the digitized ECG signal,
an improved signal-to-noise ratio of at least 15 dB as measured using the ANSI EC 57 standard, and
a quality of signal reconstruction greater than 95%.

19. The ECG device of claim 18, wherein the digitizing circuitry is configured and arranged to receive the ECG electrical signals via the ultrasonic FM sound signal.

20. The ECG device of claim 18, wherein the converter assembly includes the digitizing circuitry and the computing circuit, and is configured and arranged to output the ECG sound signals based upon the denoised ECG signal.

21. An apparatus comprising:
at least two electrodes configured and arranged to sense an ECG signal;
a denoising module communicatively coupled to the at least two electrodes and configured and arranged to receive the ECG signal sensed by the electrodes, the denoising module including:
circuitry configured and arranged to condition and digitize the ECG signal, and
a computing circuit configured to process said digitized ECG signal to denoise the ECG signal, based upon a time-based distribution of subcomponents of the signal; and
a communications circuit configured and arranged to generate a wireless communication including the denoised ECG signal for access by a device remote from the communications circuit.

* * * * *

UNITED STATES PATENT AND TRADEMARK OFFICE
CERTIFICATE OF CORRECTION

PATENT NO. : 9,414,786 B1
APPLICATION NO. : 14/032544
DATED : August 16, 2016
INVENTOR(S) : Brockway et al.

Page 1 of 1

It is certified that error appears in the above-identified patent and that said Letters Patent is hereby corrected as shown below:

In the Specification

Column 1 Line 19 Please insert the following after the Title:
--STATEMENT REGARDING FEDERALLY SPONSORED RESEARCH AND DEVELOPMENT
This invention was made with government support under HL110739 and DA041815 awarded by the National Institutes of Health.--

Signed and Sealed this
Sixteenth Day of June, 2020

Andrei Iancu
*Director of the United States Patent and Trademark Office*